US008798716B1

(12) United States Patent
DeSena et al.

(10) Patent No.: US 8,798,716 B1
(45) Date of Patent: Aug. 5, 2014

(54) FIDUCIAL MARKERS AND RELATED METHODS

(75) Inventors: Danforth S. DeSena, Cape Elizabeth, ME (US); Peter Caravan, Cambridge, MA (US)

(73) Assignee: Solstice Corporation, South Portland, ME (US)

( * ) Notice: Subject to any disclaimer, the term of this patent is extended or adjusted under 35 U.S.C. 154(b) by 0 days.

(21) Appl. No.: 13/288,481

(22) Filed: Nov. 3, 2011

(51) Int. Cl.
*A61B 5/05* (2006.01)
*A61B 19/00* (2006.01)

(52) U.S. Cl.
CPC ......... *A61B 19/54* (2013.01); *A61B 2019/5454* (2013.01); *A61B 2019/5495* (2013.01)
USPC ................... 600/414; 600/8; 600/426; 600/7; 600/3

(58) Field of Classification Search
None
See application file for complete search history.

(56) References Cited

U.S. PATENT DOCUMENTS

| | | | | |
|---|---|---|---|---|
| 4,702,228 | A * | 10/1987 | Russell et al. | 600/8 |
| 4,891,165 | A * | 1/1990 | Suthanthiran | 600/8 |
| 5,232,452 | A * | 8/1993 | Russell et al. | 604/180 |
| D341,968 | S | 12/1993 | Kumerfield | |
| 5,320,100 | A | 6/1994 | Herweck et al. | |
| 5,368,030 | A * | 11/1994 | Zinreich et al. | 600/414 |
| 5,383,234 | A * | 1/1995 | Russell | 378/164 |
| 5,505,932 | A * | 4/1996 | Grinstaff et al. | 424/9.3 |
| 5,508,021 | A * | 4/1996 | Grinstaff et al. | 424/9.322 |
| 5,508,388 | A * | 4/1996 | deLearie et al. | 534/16 |
| 5,609,827 | A | 3/1997 | Russell et al. | |
| 5,656,211 | A * | 8/1997 | Unger et al. | 264/4.1 |
| 5,702,128 | A * | 12/1997 | Maxim et al. | 283/81 |
| 5,743,899 | A | 4/1998 | Zinreich | |
| 5,763,393 | A | 6/1998 | Moskal et al. | |
| 5,773,024 | A * | 6/1998 | Unger et al. | 424/450 |
| 5,887,437 | A | 3/1999 | Maxim | |
| RE36,461 | E * | 12/1999 | Russell et al. | 604/180 |
| 6,096,048 | A * | 8/2000 | Howard et al. | 606/130 |
| 6,107,271 | A | 8/2000 | Moskal et al. | |
| 6,146,657 | A * | 11/2000 | Unger et al. | 424/450 |
| 6,200,258 | B1 * | 3/2001 | Slater et al. | 600/8 |
| 6,264,599 | B1 * | 7/2001 | Slater et al. | 600/7 |
| 6,273,851 | B1 * | 8/2001 | Slater et al. | 600/8 |
| 6,333,971 | B2 * | 12/2001 | McCrory et al. | 378/162 |
| 6,471,632 | B1 * | 10/2002 | Jahrmarkt et al. | 600/8 |
| 6,522,908 | B1 * | 2/2003 | Miyashita et al. | 600/409 |
| 6,574,497 | B1 * | 6/2003 | Pacetti | 600/420 |
| 6,666,812 | B2 * | 12/2003 | Jahrmarkt et al. | 600/8 |
| 6,687,533 | B1 * | 2/2004 | Hirano et al. | 600/426 |

(Continued)

OTHER PUBLICATIONS

Yang et al, "1 H Chemical Shift Magnetic Resonance Imaging Probes with High Sensitivity for Multiplex Imaging", Contrast Media Mol Imaging. 2012 ; 7(2): 276-279. doi:10.1002/cmmi.490.*

*Primary Examiner* — Nicholas Evoy
(74) *Attorney, Agent, or Firm* — K&L Gates LLP

(57) ABSTRACT

In part, the invention relates to fiduciary markers suitable for affixing to a patient that are detectable with respect an imaging modality such as MRI and methods of making the same. The markers include a paramagnetic material disposed therein that generates a distinguishable signal relative to a patient or other biological sample of interest during an imaging data collection session. Further, the markers demonstrate desirable signal to noise ratios across two or more MRI data collection procedures in one embodiment. The length of the markers is also adjustable by, for example, cutting or tearing a substrate upon which a substantially fluid-free region straddles a specified separation position on the substrate.

24 Claims, 24 Drawing Sheets

(56) References Cited

U.S. PATENT DOCUMENTS

| | | | |
|---|---|---|---|
| 6,712,752 B2 * | 3/2004 | Slater et al. | 600/8 |
| 6,712,844 B2 * | 3/2004 | Pacetti | 623/1.15 |
| 6,714,628 B2 * | 3/2004 | Broyles et al. | 378/164 |
| 6,826,257 B2 | 11/2004 | Sayre et al. | |
| 6,826,423 B1 * | 11/2004 | Hardy et al. | 600/429 |
| D503,980 S | 4/2005 | Sayre et al. | |
| 6,985,558 B1 | 1/2006 | Russell | |
| 6,989,015 B2 | 1/2006 | Daum et al. | |
| 7,042,219 B2 | 5/2006 | Biglieri et al. | |
| D527,820 S * | 9/2006 | Solar et al. | D24/140 |
| D528,211 S * | 9/2006 | Solar et al. | D24/158 |
| 7,127,040 B2 | 10/2006 | Sayre et al. | |
| 7,172,549 B2 * | 2/2007 | Slater et al. | 600/8 |
| 7,207,204 B2 | 4/2007 | Weber et al. | |
| 7,263,159 B2 * | 8/2007 | Russell | 378/37 |
| D552,735 S | 10/2007 | Archambault | |
| D559,985 S | 1/2008 | Dzierlatka | |
| 7,479,108 B2 * | 1/2009 | Rini et al. | 600/300 |
| 7,483,732 B2 * | 1/2009 | Zhong et al. | 600/423 |
| D590,948 S | 4/2009 | Archambault | |
| D590,949 S | 4/2009 | Broyles | |
| D598,319 S | 8/2009 | Joseph | |
| 7,578,041 B2 | 8/2009 | Weber et al. | |
| D602,590 S | 10/2009 | Dzierlatka | |
| 7,602,883 B2 | 10/2009 | Joseph et al. | |
| 7,631,449 B2 | 12/2009 | McDermott et al. | |
| 7,643,867 B2 * | 1/2010 | Solar et al. | 600/426 |
| 7,660,619 B2 | 2/2010 | Biglieri et al. | |
| 7,702,378 B2 * | 4/2010 | Bolan et al. | 600/414 |
| 7,720,522 B2 * | 5/2010 | Solar et al. | 600/426 |
| 7,736,293 B2 * | 6/2010 | Lamoureux et al. | 600/8 |
| 7,743,540 B2 | 6/2010 | McDermott | |
| 7,781,041 B2 | 8/2010 | Broyles | |
| 7,787,934 B2 | 8/2010 | Mazzocchi et al. | |
| 7,815,123 B2 | 10/2010 | Conner et al. | |
| D627,469 S | 11/2010 | Dzierlatka | |
| 7,831,293 B2 | 11/2010 | Ellis et al. | |
| 7,856,082 B2 | 12/2010 | Flynn et al. | |
| D631,547 S | 1/2011 | Sayre et al. | |
| 7,885,441 B2 * | 2/2011 | Node-Langlois et al. | 382/128 |
| 7,886,569 B2 | 2/2011 | Weber et al. | |
| 7,914,570 B2 * | 3/2011 | Brown | 623/1.22 |
| 7,925,326 B2 * | 4/2011 | Siegel et al. | 600/414 |
| D643,928 S | 8/2011 | Dzierlatka | |
| 8,012,295 B1 | 9/2011 | Broyles | |
| 8,014,575 B2 * | 9/2011 | Weiss et al. | 382/128 |
| 8,021,291 B2 * | 9/2011 | Lamoureux et al. | 600/8 |
| 8,114,007 B2 * | 2/2012 | Lamoureux et al. | 600/8 |
| 8,187,159 B2 * | 5/2012 | Lamoureux et al. | 600/8 |
| 8,366,598 B2 * | 2/2013 | Lamoureux et al. | 600/8 |
| 8,401,145 B1 | 3/2013 | Boutte | |
| D683,020 S | 5/2013 | Boutte | |
| 8,457,377 B2 * | 6/2013 | Weiss | 382/128 |
| 8,544,162 B2 * | 10/2013 | Bolan et al. | 29/460 |
| 2002/0173690 A1 | 11/2002 | Jahrmarkt et al. | 600/8 |
| 2003/0069463 A1 | 4/2003 | Jahrmarkt et al. | 600/8 |
| 2004/0236169 A1 | 11/2004 | Slater et al. | 600/8 |
| 2004/0242953 A1 * | 12/2004 | Good | 600/7 |
| 2005/0025797 A1 * | 2/2005 | Wang et al. | 424/422 |
| 2005/0074405 A1 | 4/2005 | Williams | 424/9.3 |
| 2005/0107870 A1 * | 5/2005 | Wang et al. | 623/1.44 |
| 2005/0240098 A1 * | 10/2005 | Zhong et al. | 600/410 |
| 2006/0293581 A1 * | 12/2006 | Plewes et al. | 600/407 |
| 2007/0010702 A1 * | 1/2007 | Wang et al. | 600/8 |
| 2007/0055142 A1 * | 3/2007 | Webler | 600/425 |
| 2007/0110665 A1 * | 5/2007 | Bolan et al. | 424/1.11 |
| 2007/0207186 A1 * | 9/2007 | Scanlon et al. | 424/424 |
| 2007/0223799 A1 * | 9/2007 | Weiss | 382/131 |
| 2008/0003184 A1 * | 1/2008 | Uvdal et al. | 424/9.323 |
| 2008/0044827 A1 * | 2/2008 | Bogdanov et al. | 435/6 |
| 2009/0196829 A1 * | 8/2009 | Song et al. | 424/9.35 |
| 2010/0063383 A1 * | 3/2010 | Anderson et al. | 600/411 |
| 2010/0113912 A1 * | 5/2010 | Traboulsi et al. | 600/414 |
| 2010/0254897 A1 * | 10/2010 | Frank et al. | 424/1.29 |
| 2010/0290997 A1 * | 11/2010 | Li et al. | 424/9.3 |
| 2010/0297026 A1 * | 11/2010 | Doyle | 424/9.323 |
| 2010/0322855 A1 * | 12/2010 | Chong | 424/1.65 |
| 2011/0027189 A1 * | 2/2011 | Markov et al. | 424/9.3 |
| 2011/0123078 A9 * | 5/2011 | Weiss et al. | 382/131 |
| 2012/0020538 A1 * | 1/2012 | Weiss | 382/131 |
| 2012/0184642 A1 * | 7/2012 | Bartling et al. | 523/113 |

* cited by examiner

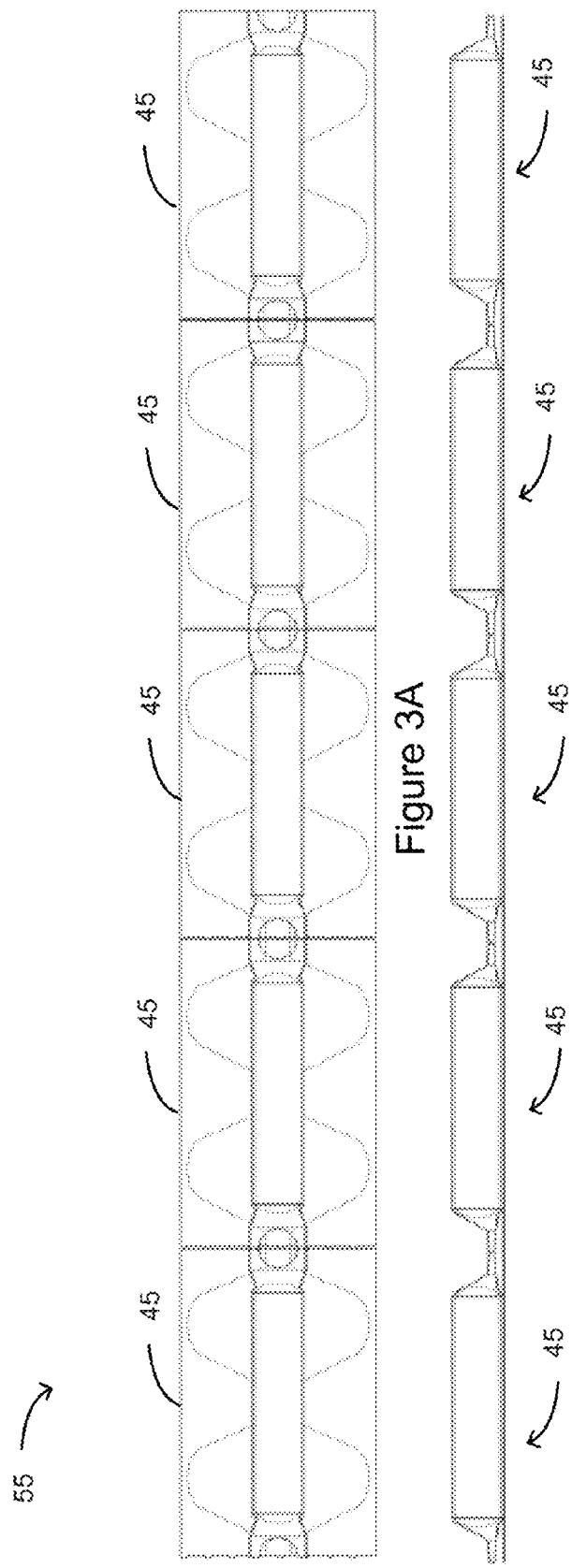

Slice thickness = 1mm
TR=7ms, TE=2.3 ms, Flip angle = 12°

0.9 x 0.9 mm
In-plane 0.4 x 0.4 mm
In-plane 0.3 x 0.3 mm
In-plane

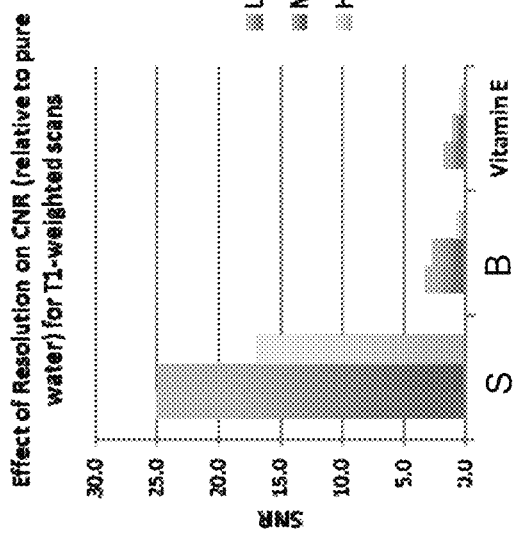
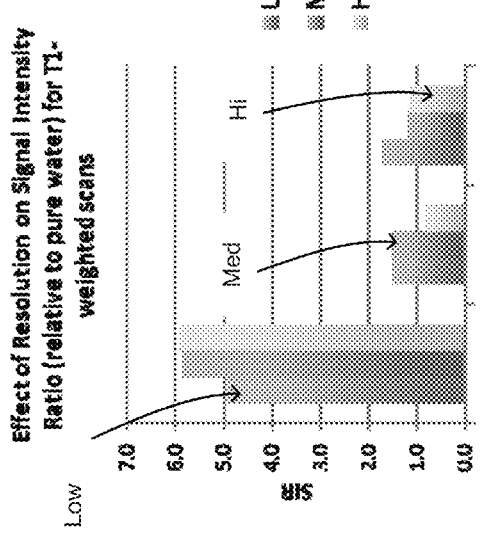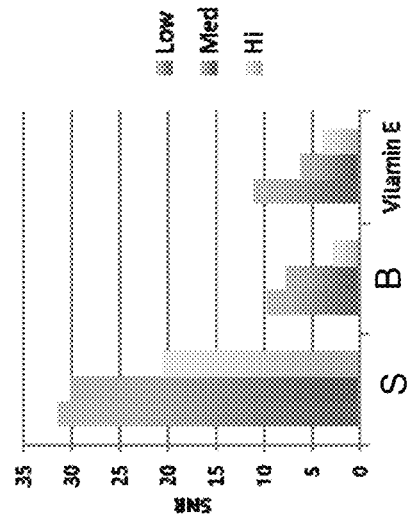
Figure 8A
Figure 8B
Figure 8C

FIDUCIAL MARKERS AND RELATED METHODS

FIELD OF THE INVENTION

The invention relates to devices, markers, methods and systems suitable for registering a position in an image or data set obtained with respect to a biological sample, such as animal tissue and anatomical structures.

BACKGROUND

Various imaging modalities are used to investigate, diagnose and treat people who may be suffering from various conditions and injuries. Photographs, X-ray, Magnetic Resonance Imaging (MRI), Ultrasound, and other imaging modalities have various advantages, disadvantages, and application specific features. Generally, with respect to a given imaging modality it is desirable for a review of any resultant images to have a reference point relative to the subject depicted in an image. Various types of coordinate schemes and markers are used to facilitate identifying positions of interest in a given image. For photographs, a grease pencil may be sufficient to indicate an area of interest such as the location for a tissue biopsy.

In the context of MRI, a magnetic field is used in concert with changing radiofrequency pulses to change the behavior of atoms in the patient's body. Those changes are tracked and transformed using various algorithms to generate an image. These different radiofrequency pulses are known as MRI acquisition types. Known MRI acquisition types include a T1 sequence, a T2 sequence, a proton density sequence. Given the complexity associated with MRI, specifying reference points using markers is more challenging.

Traditionally, vitamin E capsules have been taped to patients to reference locations in patients undergoing MRI scans. These capsules show up to varying degrees in MRI scans as a result of their lipid make up. Improvements have been made to such capsules by having a given capsule centered or otherwise disposed upon a material having a border with an adhesive material on the back.

Fabricating individual capsules and disposing them within the border of a material or substrate can be expensive as is using a lipid-based material as the filling for such capsules. Moreover, traditional capsules do not function well in all MRI radiofrequency acquisition types. Accordingly, a need exists for improved MRI, X-ray, and multi-modal markers and related methods and devices that address these issues and others.

SUMMARY OF THE INVENTION

In part, the invention relates to a fiducial marker for an imaging modality, such as for example MRI. The markers are non-invasive in one embodiment. The marker can be fabricated from a continuous tube containing signal generating material which is sealed at unit lengths in one embodiment. The marker can include a relaxation agent which is a paramagnetic material that shortens the nuclear magnetic relaxation times of atoms in nearby molecules. In one embodiment, the relaxation agents used in a given marker design can be any soluble paramagnetic material. The segmented and repeating nature of multiple markers connected end to end can allow the end user to easily tear the marker to the length appropriate for the clinical exam being conducted. This embodiment of the invention addresses the need for a linear MRI marker capable of being deployed at variable length appropriate to the clinical situation. In addition, the MRI marker can be fabricated in a continuous "web type" process on a relatively low cost base compared to individual capsule filling and fabrication.

In part, one embodiment of the invention relates to a MRI marker which a user can size along the length dimension immediately prior to a procedure. The continuous linear markers are self-aligning in that the attachment point of the two or more markers defines a ray or line segment along which the marker is aligned as opposed to capsules which are placed individually by hand and require a ruler or other mechanism to align along a ray or line segment or at consistent distance intervals.

In part, one embodiment of the invention relates to a marker such as a fiducial marker. The marker includes a flexible membrane having a thickness (M); a cavity defined by the first flexible membrane having a volume (V); and an aqueous solution including a concentration of paramagnetic material sufficient to increase a signal to noise ratio of the marker in an image, the aqueous solution disposed in and substantially filling the cavity, the aqueous solution filled cavity having an interior three-dimensional shape including a length (L), a width (W), and a height (H). The aqueous solution can be configured to have a signal intensity ratio of an intensity signal of the fiducial marker relative to an intensity signal of water greater than about 2 during at least one MRI sequence. The MRI sequence can be selected from the group consisting of a T1 weighted sequence, a T2 weighted sequence, and a proton density sequence. The signal intensity ratio of the intensity signal of the fiducial marker relative to the intensity signal of water can be greater than about 1.1 during a proton density weighted MRI sequence. The paramagnetic material can include gadolinium and the aqueous solution can have a concentration of gadolinium that ranges from about 0.01 mM to about 10 mM. The paramagnetic material can include gadolinium and the aqueous solution can have a concentration of gadolinium of about 2.7 mM, about 1.3 mM, or about 0.65 mM. The fiducial marker can include a second cavity defined by the flexible membrane and a terminal seal formed from the flexible membrane, wherein the second cavity is substantially filled with the aqueous solution, wherein the second cavity is adjacent to and releasably connected to the terminal seal.

In one embodiment, the marker can further include an elongated substrate wherein the flexible membrane is attached to a plurality of equally spaced regions of the elongate substrate. The marker can include an MRI imaging solution and a second flexible membrane, wherein second flexible membrane is substantially adjacent to the first membrane. The marker can include a hole configured to receive a needle, wherein the hole is defined by the flexible membrane. The marker can further include a plurality of cavities, linked together by a plurality of sealed sections of the flexible membrane such that the plurality of cavities are substantially co-linear, the plurality of cavities being substantially filled with the aqueous solution and having substantially the same dimensions V, W, L and H. The marker can have a cross-section having a cross-sectional shape and wherein the cross-sectional shape is selected from the group consisting of substantially cylindrical, substantially toroidial, substantially spherical, substantially tubular, substantially polyhedronic, substantially rectangular, substantially pyramidal, substantially conical, a conic section, substantially cubic, substantially triangular, substantially circular, substantially square, substantially rectangular, substantially trapezoidal, irregular, arctuate, and substantially cylindrical.

The marker can have dimensions that can vary over various ranges suitable for a given patient application. In one embodiment, M ranges from about 0.010" to about 0.050"; L ranges from about 0.2 cm to about 30.0 cm; W ranges from about 0.1 cm to about 1.5 cm; and H ranges from about 0.1 cm to about 1.5 cm. In one embodiment, M is about 0.031"; wherein L is about 0.5 cm wherein W is about 1.6 mm; and H is about 1.6 mm. The flexible membrane can include a thermoplastic elastomer. The interior three-dimensional shape of the aqueous solution filled cavity can be selected from the group consisting of substantially spherical, elongated and substantially cylindrical, and elongated and substantially rectangular. The flexible membrane can be sealed to form a first end and a second end, wherein each of the first end and the second end tapers at an angle and terminates in a substantially aqueous solution-free region. The marker can include a substrate that includes a support layer and a pressure sensitive adhesive layer disposed below the support layer wherein the flexible membrane is attached to the support layer. The aqueous solution can be configured to have a first signal intensity ratio relative to water that is greater than a second signal intensity ratio relative to water of a reference marker in at least one MRI sequence.

In one embodiment, the reference marker can selected from the group consisting of a marker comprising water; a marker comprising an alcohol; a marker comprising a lipid; a marker comprising a substantially metal-free marker; a substantially paramagnetic material-free marker; a marker consisting of water; a marker consisting of an alcohol; a marker consisting of a lipid; a marker consisting essentially of water; a marker consisting essentially of an alcohol; and a marker consisting essentially of a lipid.

In one embodiment, the marker material is substantially free of one or more visible bubbles. The marker can have a signal intensity ratio relative to water that is greater than about 2 and less than about 6 for a T1 weighted MRI scan. In one embodiment, at least two of the length (L), the width (W), and the height (H) are of the marker substantially equal. The aqueous solution can further include a substantially radiopaque material. In one embodiment, the substantially radiopaque material includes $BaCl_2.2H_2O$, wherein the concentration of $BaCl_2.2H_2O$ by weight per unit volume ranges from greater than about 0% to less than about 50%.

In one embodiment, the invention relates to a method of modulating signals in a fiducial marker during an MRI data collection session. The method includes the steps of receiving a first plurality of MRI signals directed to a sample during a first type of MRI sequence from a location external to the sample, wherein an aqueous solution comprising a paramagnetic material positioned at the location to receive a portion of the first plurality of MRI signals; emitting a first plurality of location specific signals having a first signal intensity from the aqueous solution in response to the first plurality of MRI signals; receiving a second plurality of MRI signals directed to the sample during a second type of MRI sequence, wherein the aqueous solution comprising the paramagnetic material is positioned at the location to receive a portion of the second plurality of MRI signals; and emitting a second plurality of location specific signals from the aqueous solution having a second signal intensity in response to the second plurality of MRI signals, wherein a signal intensity ratio comparing one of the first or second signal intensity to a signal intensity of water is greater than about 2. The first plurality of location specific signals and the second plurality of location specific signals can originate from within the fiducial marker. The first type of MRI sequence or the second type of MRI sequence can be selected from the group consisting of a T1 weighted sequence using TSE and a T1 weighted sequence using GRE.

In one embodiment of the invention, the marker material includes a solvent such as an aqueous solution including one or more paramagnetic materials.

In one embodiment of the invention, the non-invasive fiducial marker includes an elongated substrate that can include one or more layers. In one embodiment, the elongate substrate comprises a cellulose based layer, a pressure sensitive adhesive layer and a plastic or paper tape.

In one embodiment, the marker comprises a solution or material that is conspicuous for at least three or more different MRI image acquisition types. In one embodiment, the solution used in a given marker embodiment can be color coded based on the parameters of the solution and/or its suitability for a particular imaging purpose.

In one embodiment, the markers described herein are configured to be brighter than a tissue type selected from the group consisting of muscle, liver, kidney, grey or white matter, fat, any solid tissue in at least three or more different MRI image acquisition types.

In one embodiment, a solution is configured for use in each marker such that its signal to noise ratio is better than a lipid-based fiducial marker in at least one MRI sequence such as a T1 sequence, a T2 sequence, a proton density sequence and other similar or complementary sequences. In one embodiment, the fiducial markers have a signal to noise ratio that is significantly better during a T1 MRI data collection session when compared to metal-free water and about the same as metal-free water during a T2 or proton density MRI data collection session.

In one embodiment, the signal intensity ratio of given marker embodiment relative to pure water is greater than about 1.1 and in another embodiment the signal intensity ratio relative to water is greater than about 2. In one embodiment, the signal intensity ratio relative to water of given marker embodiment is about 4.3 when imaged using a turbo spin echo T1-weighted sequence. In one embodiment, the signal intensity ratio relative to water of given marker embodiment is about 5.5 when imaged using a T1-weighted gradient echo sequence.

In one embodiment, the marker material is substantially free of air bubbles such as by visible inspection. The presence of air bubbles in a fiducial marker can be problematic for an MRI scan. This follows because if a MRI slice passes through an air bubble in the marker, the air bubble creates a so-called susceptibility artifact that causes signal loss that is actually larger than the bubble itself. Thus, air bubbles can causes shadows or other imaging artifacts. These shadows or artifacts may result in obscuring the marker, which is problematic and a safety risk to a patient. Given that one reason for using the markers is to create a visible reference point for a clinician, removal of air bubbles improves marker function, marker aesthetics and addresses clinical safety concerns.

In one embodiment, the material inside tube is designed to be visible not only on MRI but simultaneously visible on CT and/or X-ray. For example, a hydrocolloid of water and carboxymethylcellulose with 25% $BaCl_2$ and equivalents and variations thereof can be used in one embodiment. In addition, $BaCl_2$ can also be used in various embodiments as part of the same marker material containing a paramagnetic material or in a separate cavity disposed adjacent to or otherwise near the paramagnetic material. Other Barium containing solutions or materials and other materials suitable for improving detection during an X-ray scan can be used.

The markers described herein can also be designed for ingestion by a user to provide a reference point when collecting image data with respect to the gastrointestinal system or as an internal reference within the body cavity. Thus, the markers can be designed to include a membrane that is acid resistant and suitable for swallowing. In one embodiment, a combination of a X-ray and a MRI imageable marker material can be disposed in such a marker.

This Summary is provided merely to introduce certain concepts and it is not intended to identify any key or essential features of the claimed subject matter.

BRIEF DESCRIPTION OF DRAWINGS

The figures are not necessarily to scale, emphasis instead generally being placed upon illustrative concepts. The figures are to be considered illustrative in all aspects and are not intended to limit the invention, the scope of which is defined only by the claims.

FIG. 3A shows a top view of five connected fiducial markers disposed on five substrates to, in part, illustrate the ability to tailor marker length in accordance with an illustrative embodiment of the invention.

FIG. 3B shows a side view of the fiducial markers and substrates of FIG. 3A in accordance with an illustrative embodiment of the invention.

FIGS. 8A-8C are plots demonstrating the effect of spatial resolution on signal intensity ratio, contrast noise ratio, and signal to noise ratio, respective, obtained during three T1 weighted MRI data collection sessions with respect to two conventional marker solutions and a marker material in accordance with an illustrative embodiment of the invention.

DETAILED DESCRIPTION

Figure 1A:
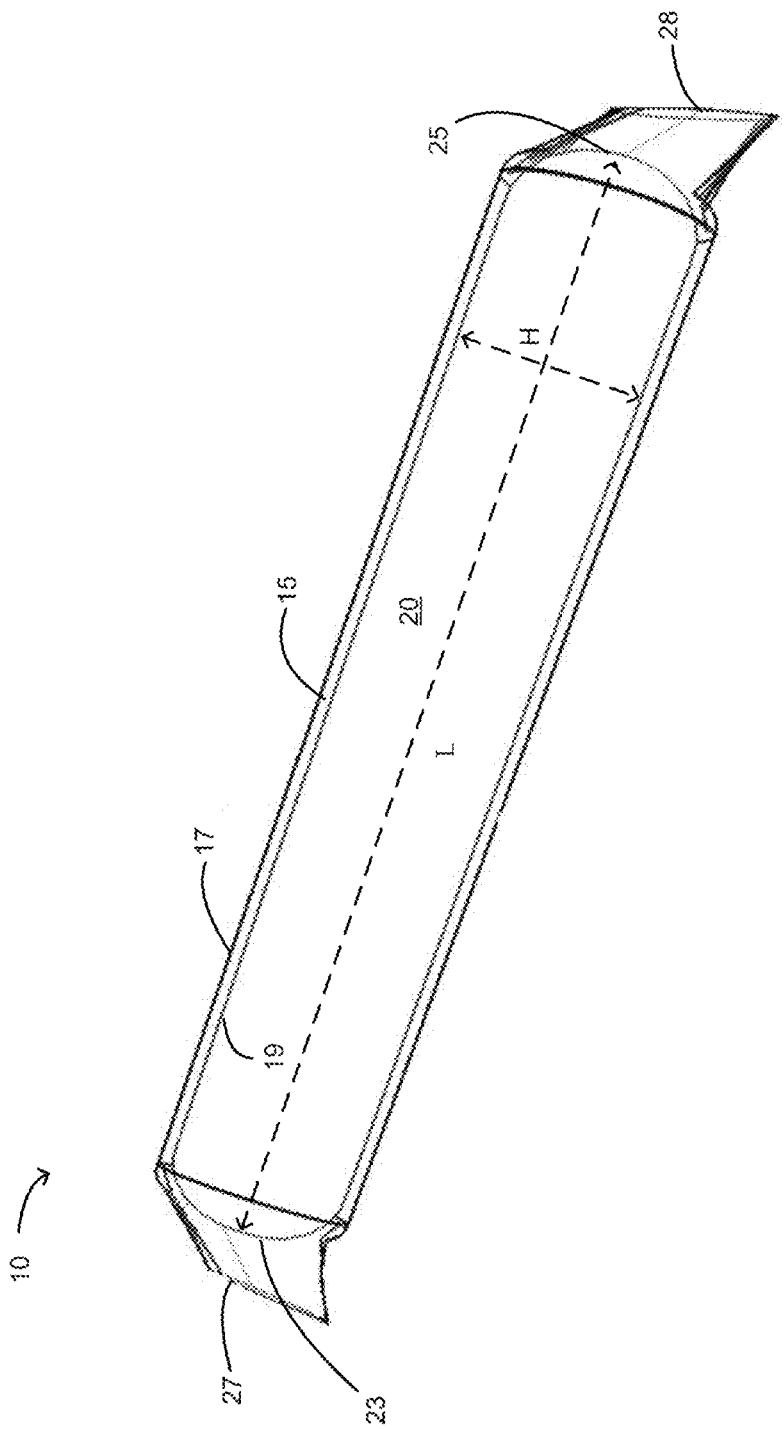
FIG. 1A shows a perspective view of a fiducial marker in accordance with an illustrative embodiment of the invention.

In part, the invention relates to fiducial markers configured for use with one or more imaging modalities such as MRI, CT or CAT Scans, other X-ray scans and combinations thereof. The markers can be of various sizes and shapes. In one embodiment, the markers include a shell or membrane that defines a cavity suitable for containing a marker material. The marker material can be a solid, liquid, gel or other suitable state or phase of matter. Paramagnetic materials and substantially radiopaque materials can be used to make multi-modal markers that exhibit desirable contrasts levels and signal intensity during both MRI and X-ray scans.

Liquid or semi-solid marker materials can allow suitable compounds to be solvated therein. This can result in unwanted contaminants being incorporated into the marker during manufacture. Air or other gas contaminants can degrade an MRI signal or otherwise cause imaging artifacts. As a result, one embodiment of the invention relates to markers that include a marker material or marker that is or appears substantially bubble free.

Further, the marker material can be configured to have an improved contrast level or resolution through the incorporation of one or more compounds. As a result, the size of the markers can be reduced relative to existing marker offerings. Making smaller markers, such as small annular or spheroidal markers is a challenge. Enabling a small volume of marker material to exhibit a higher contrast level is significant because it allows the entire marker to be smaller. In addition, removing visible bubbles from small and larger markers improves their efficacy as fiducials and helps reduce the likelihood of a smaller marker not showing up in an image. Overcoming these challenges is a limitation of various conventional marker designs.

In part, the invention also relates to continuous fiducial markers configured to be adjustable such that the length of the continuous marker is variable. Multiple markers can be used in a continuous strip to facilitate outlining or targeting a region of interest for a given imaging modality. For example, in one embodiment, instead of each marker being individual capsules that are each surrounded by the border of a backing material, a marker described herein can be formed using a length of tubing such as a fillable membrane. This feature of the invention enables continuous linear or coaxial markers to be fabricated. In contrast with conventional markers that by design must include gaps between the individual discontinuous border sections at the edges of the material upon which the marker is disposed, a continuous linear or coaxial marker includes connected segments disposed continuously on a substrate. The substrate can include a strip of material such as tape with perforated sections at one or both edges of a segment. Such continuous markers are easier for users to apply to a patient and apply in a precise manner relative to the area of interest. For example, if a user desires to place a 4" by 4" square over an area of interest of a patient, this can be done by measuring and then tearing four continuous strips of one of the marker embodiments described herein.

In part, the invention also relates to markers suitable for use during different MRI data collection procedures such as T1 weighted, T2 weighted, proton density sequences and others that are easier to detect relative to conventional lipid-based markers or other types of markers that include water or alcohols such as propylene glycol. This improved responsiveness and/or detectability across different MRI data collection procedures makes it suitable for a user to affix it to a patient and then proceed to image the marker across multiple MRI data collection sessions or other imaging modes such as an x-ray scan or data collection session.

T1, T2, and proton density (PD) weighted images are by far the most common types of images generated using MRI. In most biomedical MRI applications, water and mobile lipids are detected. However, in different biochemical and physiological environments, water can have different magnetic properties. In turn, these differences can be exploited to produce different contrast levels in images generated using magnetic resonance (MR). Differences in the amount of water or lipids (proton density), differences in the T1, T2, T2*, or T1rho relaxation times, differences in diffusion, differences in chemical shift, differences in blood flow, and differences in signal phase between two tissue types have all been used to create MR image contrast. The most common techniques are image acquisitions weighted to T1, T2, or proton density using gradient echo (GRE) or spin echo (SE) data acquisitions.

T1, T2, and proton density weighted image acquisitions are distinguished by the scanner settings repetition time (TR) and echo time (TE). T1 weighted scans have short TR and short TE. T2 weighted scans have long TR and long TE. Proton density weighted images have long TR and short TE. Different acronyms are used in the literature and on different manufacturer's platforms. These include, but are not limited to spoiled gradient recalled echo (SPGR), fast spin echo (FSE), turbo spin echo (TSE), half Fourier single shot turbo spin echo (HASTE), fast field echo (FFE), fast low angle shot (FLASH), gradient and spin echo (GRASE), Steady-State Free Precession (SSFP), Fast Imaging with Steady-state Precession (FISP) and balanced FISP (TrueFISP), Gradient Recall Acquisition using Steady States (GRASS), Fast Field Echo (FFE) and balanced FFE (b-FFE), Fast Imaging Employing Steady-state Acquisition (FIESTA), T1 High Resolution Isotropic Volume Excitation (THRIVE), Volume Interpolated Breathhold Examination (VIBE), and Magnetization Prepared RApid Gradient Echo Imaging (MP-RAGE). Embodiments of the invention are configured to operate with one or more or all of these analogous or modified versions of T1, T2, and proton density weighted MRI data acquisition processes.

Notwithstanding the foregoing, improvements in the detectability of the marker result, at least in part, due to the selection of a solid material, gel, aqueous solution, solvent, or other material in combination with one or more relaxation agents which can include paramagnetic materials. Accordingly, these materials and combinations thereof are not limited for use in continuous linear or coaxial markers, but rather can also be used in discontinuous capsule-shaped markers and other suitable markers.

In addition, the fiducial markers described herein are configured to have improved signal to noises ratios when imaged using an MRI procedure such as the T1, T2, proton density sequence, or other similar or equivalent sequences. In one embodiment, water can be used as a reference or standard to which marker contrast levels can be evaluated across different scans. For example, as discussed in more detail below, in one embodiment marker designs of the invention have signal intensities that can be compared to the signal intensity of water. In this manner, signal intensity ratios relative to water can be obtained on a per marker basis for different MRI sequences. These ratios can then be used to differentiate markers. FIG. 6D provides such a comparison.

With the foregoing as an overview of some of the general features of different embodiments of the invention, additional details follow from considering the various figures, images, and charts described below.

FIGS. 1A to 1E illustrate details of a fiducial marker 10 alone or connected to one or more fiducial markers. These markers and others described herein can be affixed to a patient at a point or area of interest such that during an imaging data collection session the marker shows up as a reference or a fiducial point having a detectable contrast level and shape. In FIG. 1A, the marker 10 has an elongate or tubular geometry. A membrane 15 which can be flexible or rigid has an outer surface 17 and an inner surface 19. A marker material 20 is disposed in the cavity defined by the membrane 15. This cavity has a height H and length L. Although depicted as regular and substantially tubular or cylindrical, the marker 10 can have various shapes as permitted by filling a membrane with a liquid or other type of material. Other embodiments can use capsule and other conventional materials to contain the marker material 20. In one embodiment, the membrane includes a flexible, malleable, heat-sealable, thermoplastic elastomer.

The cavity bounded by surface 19 has a first internal end face or surface 23 and a second internal end face or surface 25. The outer surface 17 terminates at a first terminus or edge 27 and a second terminus or edge 28. As shown, some portion of the marker 10 between each internal surface 23, 25 and each edge 27, 28 are substantially free of marker material. This occurs in some embodiments as a result of the marker material 20 being sealed by crimping, heating, melting, fusing, or otherwise sealing the marker material within the cavity defined by surface 19.

The marker material can include aqueous solutions, solutions, lipids, relaxation materials, paramagnetic materials, and other materials. These materials can be used to form the marker without a membrane if solid enough at room temperature to remain affixed to a patient during a data collection session. Alternatively, these materials can be dispersed, dissolved, solvated, or otherwise mixed with a liquid, semisolid, gel, matrix or other material to form the marker 10 or the marker material 20.

As shown in FIG. 1A, the marker material 20 has a substantially cylindrical geometry along a center region moving outward along the longitudinal axis to the ends of the marker. Although the marker 10 is shown as having curved end faces 25 and 23, these surfaces can have any suitable geometry, including for example a circle, oval, square, triangle, pentagon, etc. The membrane 15 tapers at an angle to an edge as shown. These angles can vary but are typically between 0 and 90 degrees and more preferably between 30 and 60 degrees.

In one embodiment, the marker material 20 includes air bubbles that move relative to the inner membrane 19 of the marker 10. Preferably in one embodiment the marker material 20 or the cavity defined by surface 19 is substantially free of undissolved gas or bubbles. In one embodiment, a fiducial marker 10 is fabricated using an elongated tubular member filled with material 20 and then selectively compressed and heated at either end to form individual fiducial markers. The tapering results from the compressing and pressure or thermal bounding of the membrane 15 to itself in one embodiment. The repeating pattern of the tapered sections rising to a peak formed by the top section of a marker and then tapering again followed by a subsequent rise traces a serpentine or oscillating pattern along the length of some embodiments of the continuous linear marker.

Figure 1B:
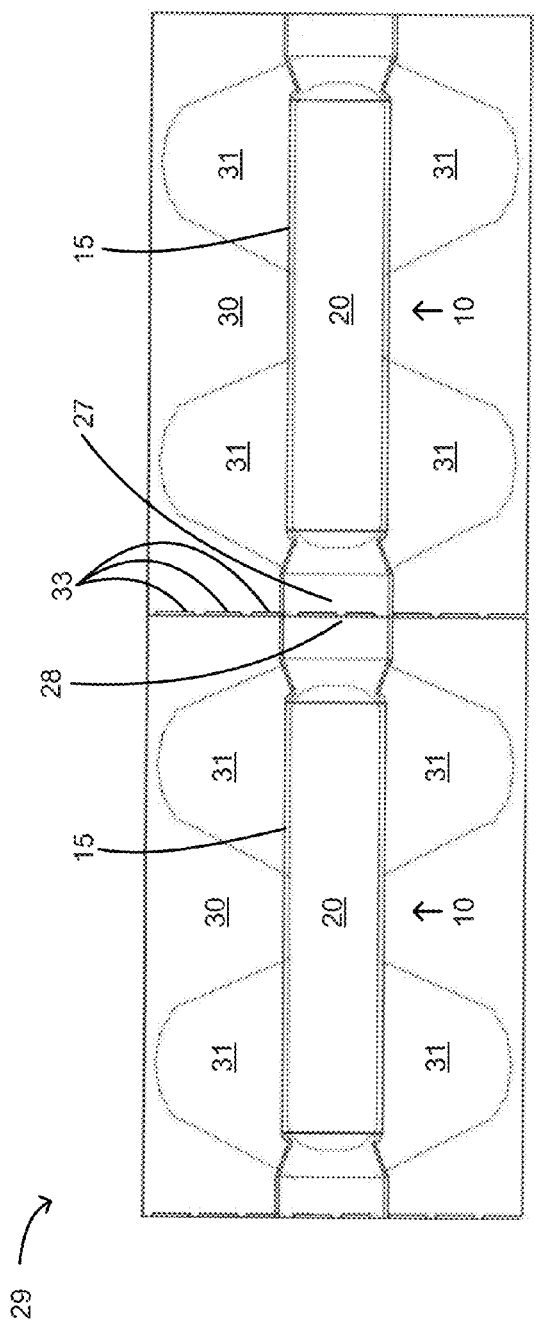
FIG. 1B shows a top view of two connected fiducial markers disposed on two substrates in accordance with an illustrative embodiment of the invention.
Figure 1C:
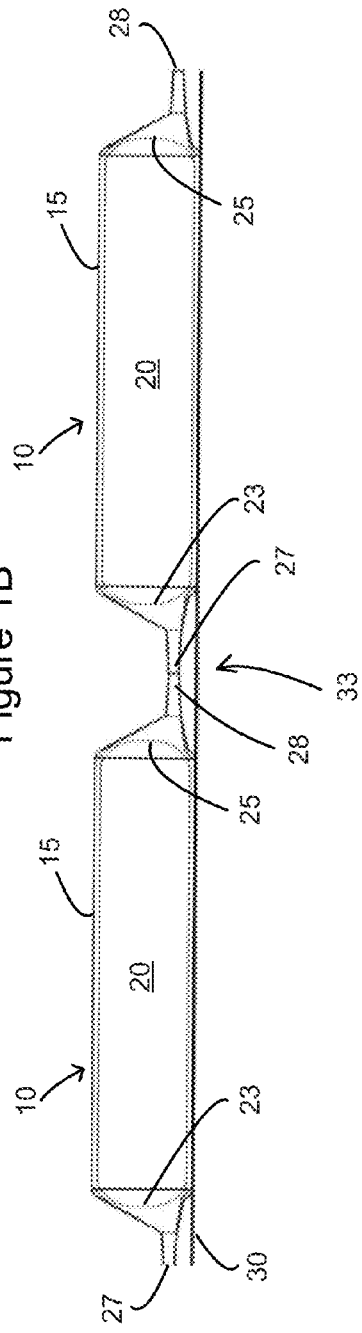
FIG. 1C shows a side view of the markers of FIG. 1B in accordance with an illustrative embodiment of the invention.

As shown in FIG. 1B, in one embodiment, the invention relates, in part, to a continuous marker 29 that can be adjusted lengthwise. This adjustment is performed by selecting as many markers as needed and then cutting or otherwise separating them from the rest of the markers at, e.g., edge 28. The markers are typically connected and thus form a continuous linear arrangement. As shown, the continuous marker includes two of the markers in a connected configuration using the marker 10 from FIG. 1A as an exemplary embodiment. In alternative embodiments edge 28 may be perforated, creased or alternatively configured to aid in the separations of marker segments 10.

The various marker embodiments described herein may be attached to or disposed on a substrate 30 such as a cellulose polymer, plastic or other suitable substrate. The substrate can include a plurality of layers such as a support layer and an adhesive layer. A paper, plastic, polymer, synthetic material, or cardboard tape can be used as the substrate 30. A substrate 30 with an adhesive such as a pressure sensitive adhesive disposed underneath and affixed to a release backing is desirable because it allows one or more markers 10 to be conveniently measured and attached to a subject. The substrate 30 can have an elongate or other irregular or rectilinear shape.

Figure 1D:
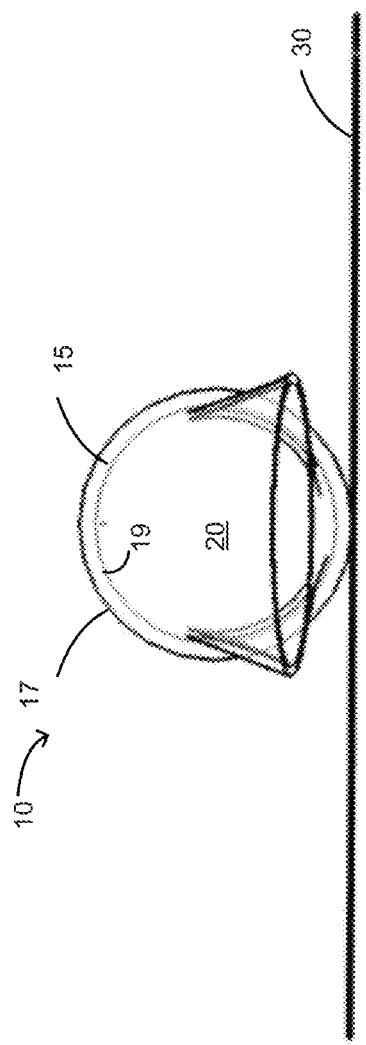
FIG. 1D shows an end view of one fiducial marker in accordance with an illustrative embodiment of the invention.

Various sources of visual or tactile information 31 such as logos, marker data, color codes, and other information can be printed, formed, and otherwise encoded on each substrate 30 or on marker 10. As shown, in FIG. 1B, in one embodiment, substrate 30 is perforated to define rectilinear units or other shaped units upon which a marker 10 is disposed. The perforations 33 are formed in the substrate 30 and aligned with the edges 27, 28 as shown. Typically, the markers 10 are formed in a continuous strip and remain so attached. The edges 27, 28 of a given marker 10 straddle and are aligned above the perforation 33 between the substrates 30. The region of the membrane 15 above the perforation 33 can be scored or pre-cut to facilitate separation of two markers 10 at the membrane 15 junction. The tapering of the membrane 15 as it approaches the substrate 30 is shown in FIG. 1D.

Figure 1E:
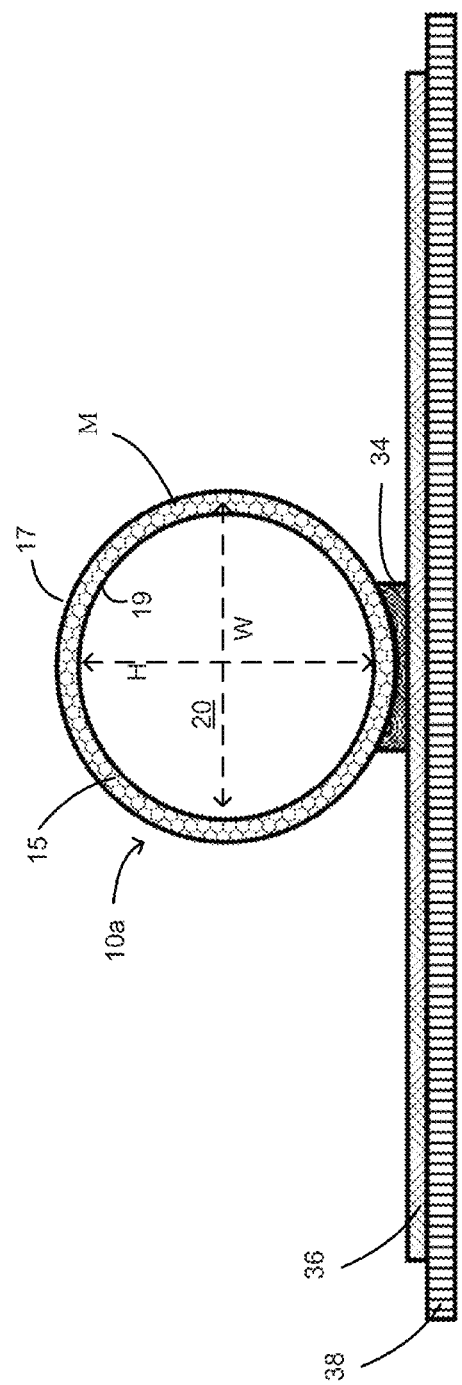
FIG. 1E shows a cross-sectional view at or around the midpoint of one fiducial marker in accordance with an illustrative embodiment of the invention.

In FIG. 1E, a fiducial marker 10a is shown. The height H and width W are shown. These dimensions can be the same or vary as can the cross-section of the marker 10a. The membrane 15 has a membrane thickness M which can vary or be tailored for a particular application. As shown, the marker 10 is attached by an adhesive or other attachment mechanism 34 to a support layer 36 which has a backing material 38 disposed below it. An adhesive layer, not shown, can be attached to the backing layer. This adhesive layer can be activated such as by removing a releasable liner not shown prior to applying the adhesive layer to a subject. In one embodiment, fiducial marker 10a has the same geometry of marker 10 shown in FIG. 1A. In another embodiment, marker 10a can be a substantially spherical marker having a substantially circular cross-section such as marker 85 shown in FIG. 5A.

Figure 2A:
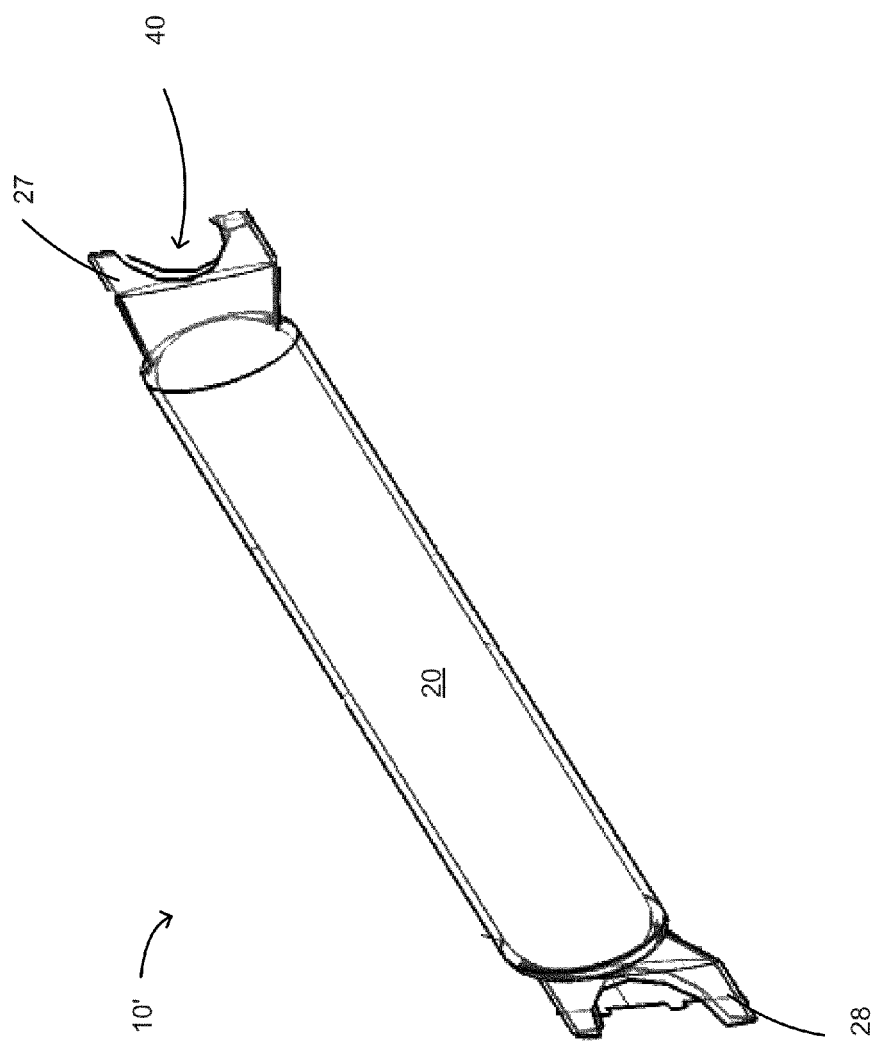
FIG. 2A shows a perspective view of another fiducial marker having a terminal end configured to form a fraction of an opening in accordance with an illustrative embodiment of the invention.
Figure 2B:
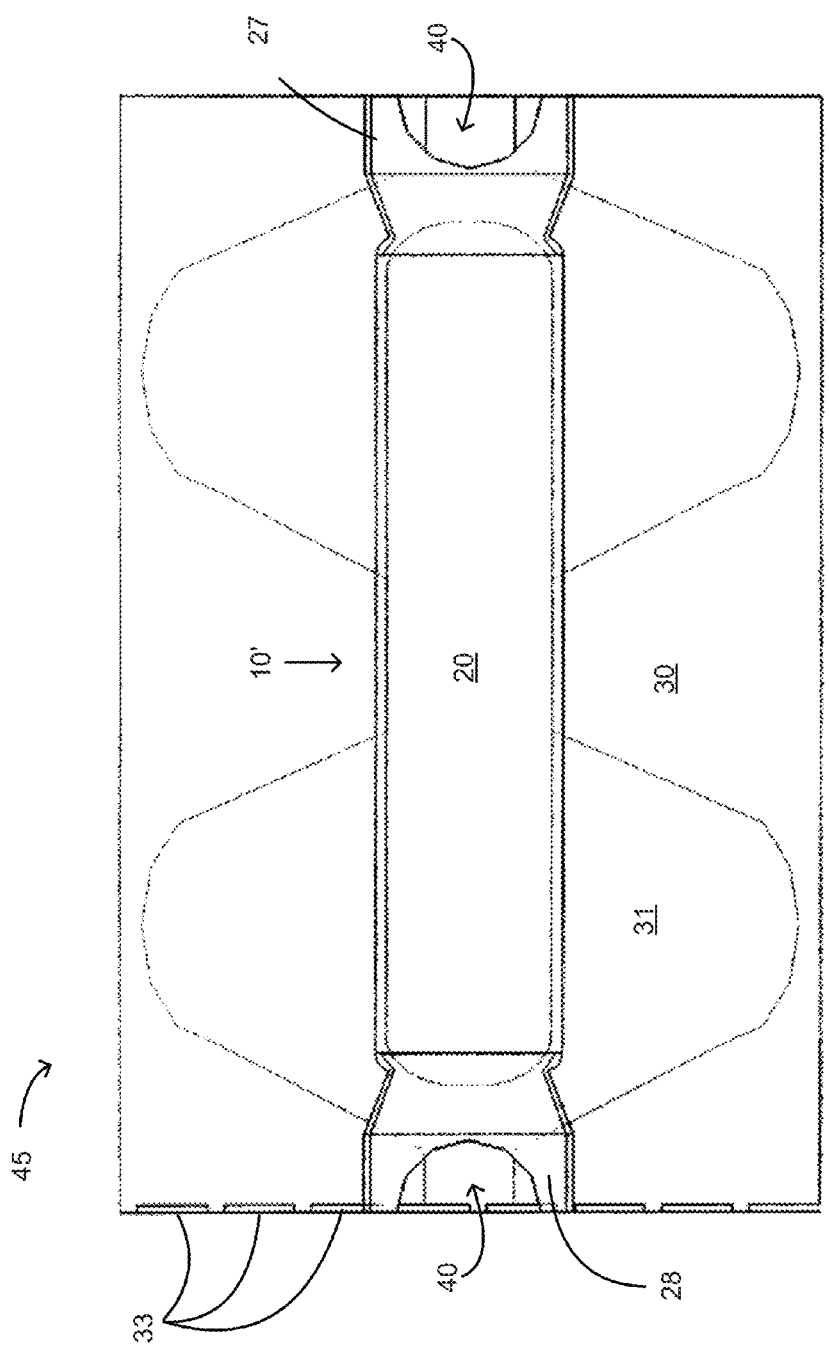
FIG. 2B shows a top view of the fiducial marker of FIG. 2A disposed on a substrate marker in accordance with an illustrative embodiment of the invention.
Figure 2C:
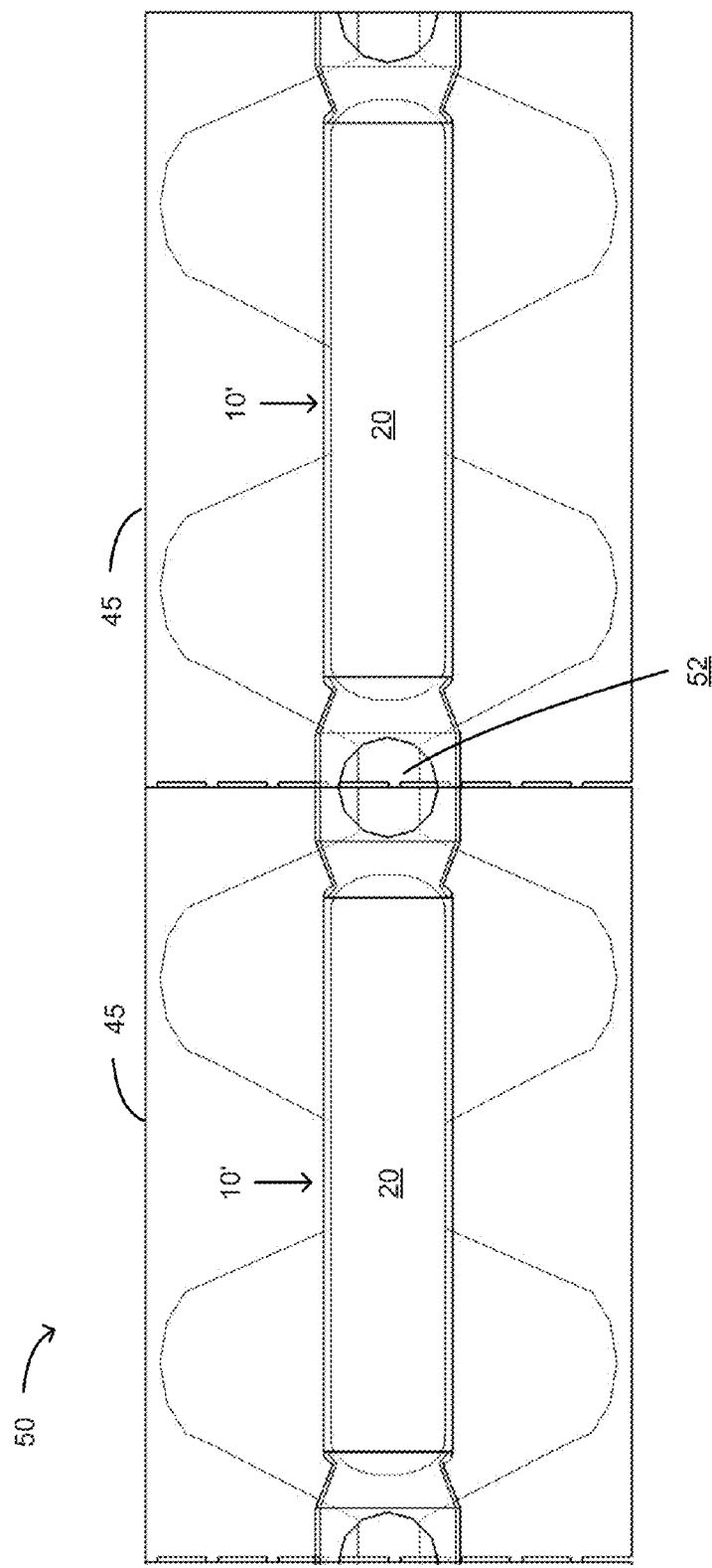
FIG. 2C shows a top view of two connected fiducial markers disposed on two substrates in accordance with an illustrative embodiment of the invention.

FIG. 2A shows another marker 10' which is a variation based on marker 10 of FIG. 1A. This marker 10' is modified such that the edges 27 and 28 are shaped by edge 40 as shown. Specifically, the edges of the marker 10' are modified such that when two markers are connected a particular shape is defined. In one embodiment, the shape is a hole suitable for receiving a surgical tool, probe, a needle or other medical implement. FIG. 2B shows a unit of a continuous fiducial marker 45 having marker 10' disposed on a substrate 30. In FIG. 2C, a continuous fiducial marker 50 is shown with two markers 10' connected and disposed on connected substrates. The combined shape 52 is now visible as a combination of two edges 40.

Figure 3C:
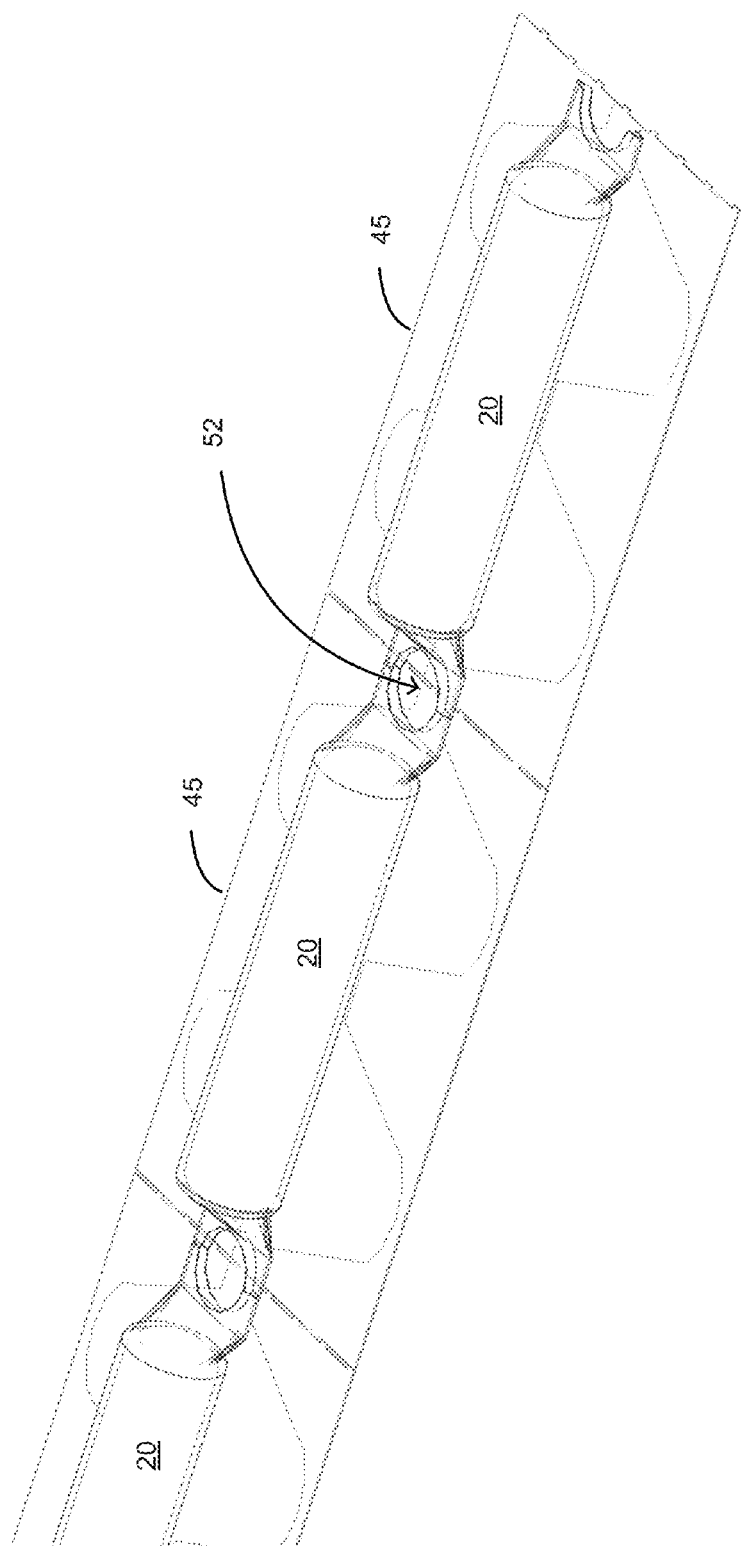
FIG. 3C shows a perspective view of the end of FIG. 3A in accordance with an illustrative embodiment of the invention.
Figure 3D:
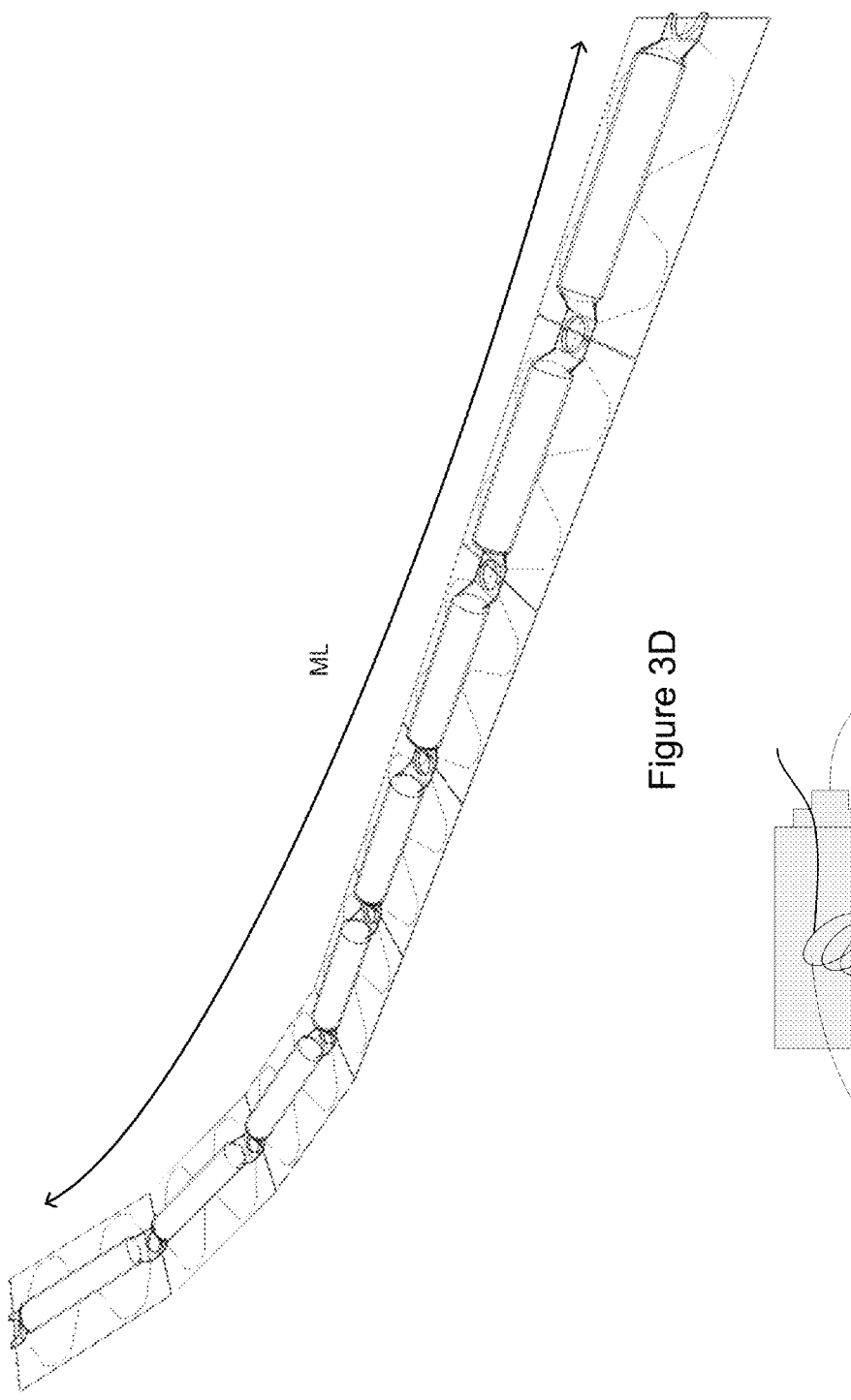
FIG. 3D shows a perspective view of a flexible continuous sequence of fiducial markers in accordance with an illustrative embodiment of the invention.

FIGS. 3A and 3B show a longer continuous fiducial marker 55 that includes units or segments 45. This marker 55 can be shortened or lengthened at the discretion of the clinician or technician marking locations on a subject prior to imaging. FIG. 3C shows a perspective view that emphasizes shape 52 where, for example, a needle may be used to inject the patient. In addition, FIG. 3D shows an even longer continuous fiducial marker having a marker length ML that includes eight markers. Although the markers shown include shape 52 and partial shapes 40, the marker 10 of FIG. 1A can also be used in these embodiments as well as any of the fiducial markers described herein.

In one embodiment, the marker 10' is made such that the crimped area is formed into a "donut" with thin side walls to allow it to be broken at the perforation with moderate force but also to allow for passage of a biopsy needle. Such an embodiment has various clinical applications. For example, suppose an eight unit length of marker is chosen based on the estimated clinical extent of the area of interest. The marker can be affixed to a breast over the suspected location of a tumor. If MRI sequences demonstrate the tumor is below the interval between the $3^{rd}$ and $4^{th}$ marker from the lateral potion of the image, a clinician now has a target through which to pass a biopsy needle, such as the third hole from the lateral edge of the marker strip in FIG. 3D, and penetrate the tumor. The distance between markers also allows biopsy depth to be estimated quickly in the clinical setting because the intervals on the marker are a fixed length and fixed distance apart.

In one embodiment, a marker is manufactured with a repeating interval every 1 cm. If imaging studies show the tumor about 3 cm below the skin, a user can visually estimate 3 cm on the marker and estimate the depth the needle must be advanced to reach the area to be biopsied. Current markers are individual units and therefore the distance between is variable and dependent on how the end-user affixes them.

The fiducial markers described herein can be used for various imaging modalities. In one embodiment, a membrane such as a flexible tube is filled with a solution that includes a paramagnetic material. This can be used for various MRI data collection sequences. Thus, in one embodiment, the invention relates to an adhesive backed, variable length, and linear skin marker for MRI imaging containing a material capable of generating a signal during various MRI sequences. The membrane 15 is sealed at intervals of known measurement (for example every 1 cm) within a continuous one-piece tube of a known diameter (about 0.25 mm to about 15 mm inside diameter). In one embodiment, the membrane 15 is flexible and heat sealable. The membrane or tube 15 may be clear to allow instant confirmation that it is sufficiently filled. Further in one embodiment, a clear tube or partially see-through tube is used as membrane 15 to visualize the contents which may be colored to represent specific performance characteristics.

Furthermore, the membrane 15 itself may also be color coded (either entirely, in longitudinal, or transverse bands) to represent the characteristics of the contents as noted above or the characteristics of the tube itself such as the internal diameter. The membrane 15 such as a tube 15 is heat sealed at unit intervals and a small cut(s) is made partially through the sealed portion to facilitate separation at such locations, if desired. Such a continuous membrane, sealed and containing marker material capable of generating signal of clinical value on MRI is then affixed to substrate 30 which can include a medical grade tape with pressure sensitive backing. The backing and tape are perforated such that the tape perforation and the partially cut heat sealed area are aligned. A continuous roll of fiducial markers that includes many markers on substrate segments may then be torn or cut by the user at any desired length along the perforation without loss of any of the sealed imaging material.

In one embodiment, a fiducial marker is configured using the filled membranes or other embodiments described herein in a right angle configuration. A marker having a bend such as a right angle bend is suitable for localizing deep structures. For example, a marker can include two lengths of three or more units each extending 90° from a common point. As an example use, a right angle or L-shape marker can be affixed to the abdomen with the apex of the right angle facing laterally. If an MRI demonstrated a mass located in the region identified by the bisection of a line drawn perpendicularly from the $3^{rd}$ unit on the superior length of the marker and from the $4^{th}$ unit on the inferior length of the marker, a clinician could direct a biopsy needle, plan surgical approach, direct therapeutic irradiation, or perform other procedures to the area described by the intersection of the perpendicular lines. Unlike current grid locators, this invention leaves the area of interest exposed and accessible to the clinician.

Closed shapes such as triangles and squares, each segment of which would have a fixed length and a fixed number of units can also be used. For example an isosceles triangle marker is formed with six marker units on each segment. Another triangle is formed with three units, four units, and five units on each respective segment. This latter embodiment may render unnecessary any requirement that the triangle be affixed to the skin in relation to any anatomic plane since each side is unique and each, therefore, can be used as a reference.

Figure 3E:
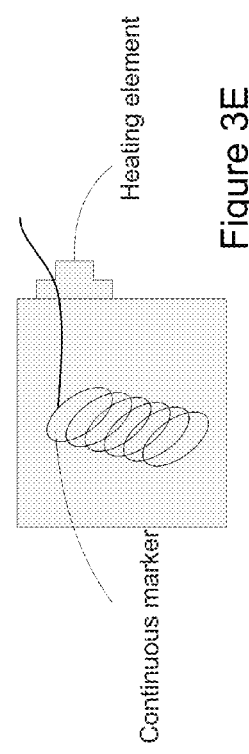
FIG. 3E shows a schematic view of a heating element for selectively sealing a flexible continuous fiducial marker in accordance with an illustrative embodiment of the invention.

In one embodiment, as shown in FIG. 3E, the fiducial marker is supplied as a long coil of tubing filled with a MRI signal generating material and sealed only at the two ends. Using a small heat sealing unit that can be part of the container in which the coil is disposed or separate therefrom, the end-user can remove a length of marker from the container and "cut off+seal" the length of their choice as needed in real time. In one embodiment, the marker material in the tube can be gelled or rendered solid or semisolid with a compound that does not change the MRI image results.

Marker Size and Shape Variations and Multi-Modal Applications

Figure 4A:
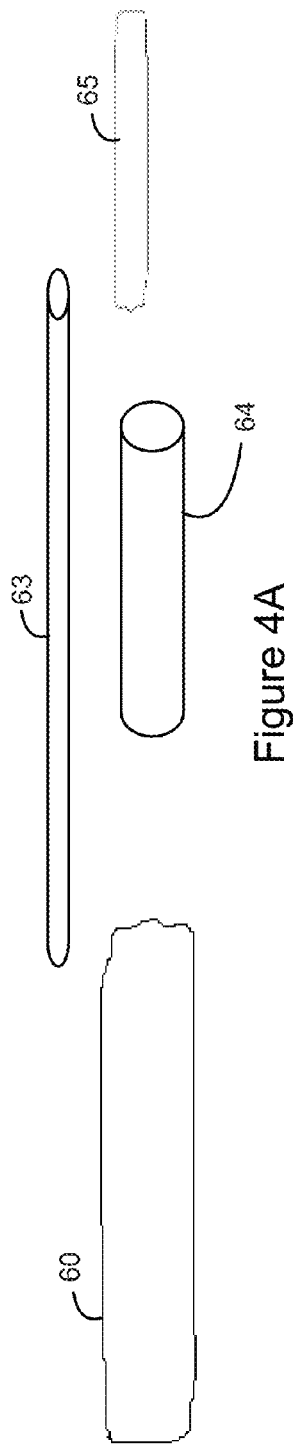
FIG. 4A shows a side view of various fiducial markers having different sizes and geometries in accordance with an illustrative embodiment of the invention.
Figure 4B:
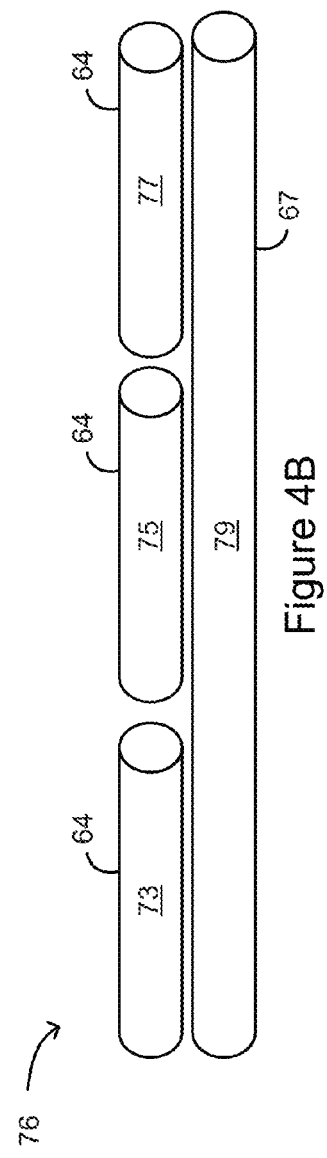
FIGS. 4B and 4C show a side view of different fiducial markers arranged in a parallel or adjacent configuration in accordance with an illustrative embodiment of the invention.
Figure 4C:
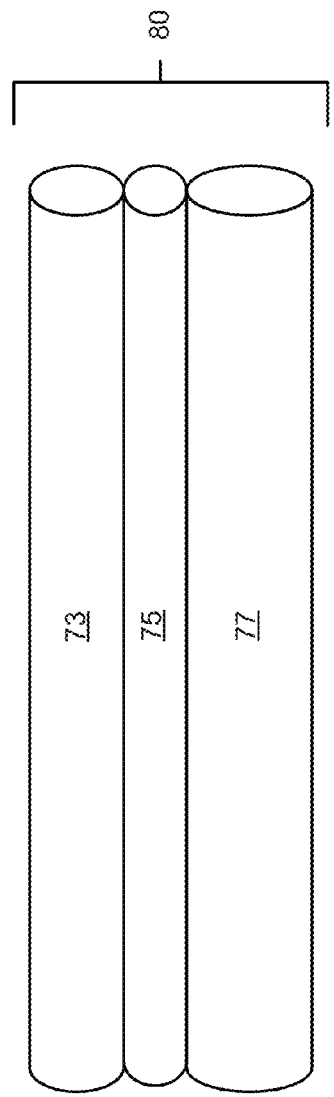

FIG. 4A shows various individual markers suitable for placing on a substrate to form a continuous linear marker. Markers 63 and 64 show that the markers can be thin or thick cylinders while markers 60 and 65 show that the markers can have an irregular surface or cross-section. These markers can include the marker materials described herein within a membrane or be made from a solid or semisolid marker material. As shown, in FIGS. 4B and 4C, multiple markers can be arranged in various parallel or proximate configurations. Thus, the longer cylindrical marker 67 can include a marker material 79. Marker 67 can be attached to or proximal to the three shorter cylindrical markers 64, but each marker 64 can have different marker materials 73, 75, 77 as shown. These marker materials can be tailored for a particular imaging regimen such as a combination of x-ray, angiography, MRI, or other modalities. These markers can include RFID elements in one embodiment. FIG. 4C shows a marker 80 that is formed using three cylindrical markers arranged in a parallel configuration with different marker materials 73, 75, 77.

Thus, in one embodiment, a marker 80, as shown in FIG. 4C, can include two or more parallel tubes, longitudinally fused together such as ribbon cable wire, each tube containing a different signal producing agent designed to excel in a specific MRI sequence (for instance one tube could have first material 73 optimized to generate robust signal during T1 sequencing, a parallel tube could contain second material 75 optimized to generate a robust signal in T2 sequencing.) A third material 77 can be tailored for a proton density sequence. This marker 80 improves visibility on all scan sequences and helps prevent the marker being mistaken for a natural linear structure such as a tendon.

In one embodiment, a marker such as marker 10 can be made from tubing. The tubing can be extruded in a cross sectional shape not likely found in nature (for example an isosceles triangular, square, or pentagonal shaped tube). This array, on cross section, would not be mistaken for a natural structure. A marker can be made with two or more tubes of different diameters, each with different signal media, aligned one within the other such as in electrical coaxial cable.

In one embodiment, a marker is made with two or more tubes of different diameters and different contents fused longitudinally in a three dimensional array such as a triangle. In one embodiment, the material inside the tube is a solution, a gel (to prevent spilling in the event of tube rupture), a colloid, or even a solid.

The markers are not limited to an elongate geometry. In some embodiment, the marker material described herein that is tailored for its signal to noise properties or multimodal imaging properties can be placed in a membrane or capsule and not used as a linear marker. Alternatively, different shaped markers may be made in quantity and disposed on an adhesive coated substrate such as a tape and used as a continuous linear marker.

Figure 5A:
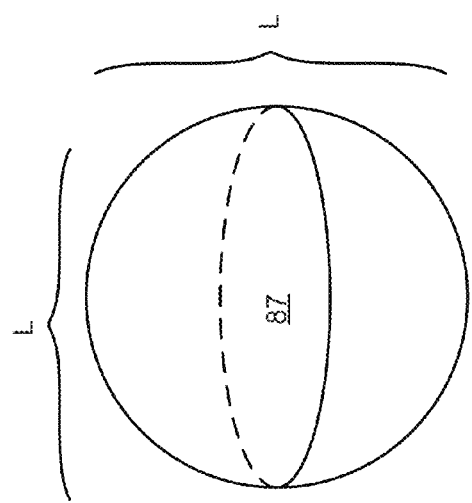
FIG. 5A shows a perspective view of a spherical fiducial marker in accordance with an illustrative embodiment of the invention.
Figure 5B:
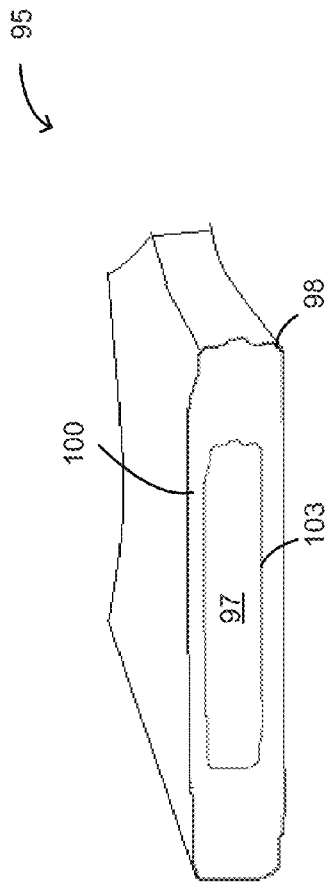
FIG. 5B shows a perspective view of a fiducial marker having a first material and a second material suitable for multimodal imaging or other uses in accordance with an illustrative embodiment of the invention.

In FIG. 5A, a marker 85 includes a material 87 that is formed into a spherical shape or bounded by a membrane, shell or other coating to maintain a particular geometry. The spherical marker 85 shown can be used individually with an attachment mechanism or can be threaded on a wire or plastic line to form a linear marker or disposed on a tape as described herein. Similarly, FIG. 5B shows a marker 95 that can have an irregular or parallelepiped shape. The marker 95 includes an outer membrane 98 and a first marker material 100. A second membrane 103 is disposed within the outer membrane 98 and the first marker material 100. A second marker material 97 is disposed within the second membrane 103. In this way, such a marker 95 can be configured such that each marker material 97, 100 is tailored for a particular data collection sequence or for use across multiple imaging scans. For example, an injured person may receive an MRI for damage to their neck and then receive a CT scan during the same hospital visit. A multimodal marker can be placed at a location of interest and then imaged using a MRI scan, CT scan, and others. Accordingly, the same marker can be used to co-register different image data sets.

Cosmetic Appearance and Gaseous Contaminant Removal

Upon reviewing conventional markers such as those offered by Beekley Corporation, upon visual inspection, one or more bubbles appear which cause the marker to have a non-uniform appearance. For example, some of the conventional markers resemble an element in a builder's level in which a bubble slides relative to an inner surface. This inclusion of air or other gas in some conventional marker results from filling and sealing a blow molded plastic ampule as part of the manufacturing process for such markers.

Apart from the visual appearance of the bubbles in the marker, which is cosmetically unappealing to some users of the markers, air or other gaseous contaminants can degrade an MRI signal or otherwise cause imaging artifacts. As a result, one embodiment of the invention relates to markers that include a marker material or marker that is or appears substantially bubble free.

Marker embodiments can be manufactured that are substantially free of bubbles using various techniques. In one embodiment, the membrane or tube used to contain the marker material is sealed with the water or the relevant solvent containing the paramagnetic material being under pressure. This results in the membrane being slightly overfilled with the marker material and/or air being driven from the water or other solvent. Similarly, the water or the relevant solvent containing or configured to subsequently receive the paramagnetic material can be boiled, cooled and sealed with the water or solvent under pressure. Other manufacturing embodiments performed at room temperature and sealed at ambient pressure or using combinations of boiling of the water or solvent can also be used. In general, a solution which is fully or sufficiently outgassed or otherwise in equilibrium can be used when filing the membrane, shell or other component of the marker to reduce or prevent bubble formation.

Marker Material and Image Data Comparison

In addition, to some of the various mechanical and structural features of the marker embodiments described herein another aspect of the invention relates to the marker material used to form or that is otherwise disposed in or on a given marker. One embodiment of the invention uses gadolinium alone or in a solution as a marker material. The inclusion of gadolinium causes a stronger MRI signal compared to the available markers on some types of MRI scans, e.g. T1-weighted. Further, given the stronger resultant MRI signal, the use of gadolinium and other materials facilitates a reduction in marker size because although there is less volume available to generate an MRI signal the stronger signal aids detection relative to the tissues of a subject. Another embodiment of the invention uses $BaCl_2$ or another substantially radiopaque material alone or in a solution as a marker material. Gadolinium can also be used with $BaCl_2$ or another substantially radiopaque material as a marker material in other embodiments.

The inclusion of $BaCl_2$ or another radiopaque material allows a given fiducial marker to be imaged with a higher contrast level during an X-ray-based scan, such as a CT scan. BaSO4 is insoluble. Accordingly, if this material were used with the Gd solutions, there would be two phases. In one embodiment, a soluble radioopaque material such as $BaCl_2$ can be a component of the marker material 20. Another embodiment of the invention increases the contrast during X-ray based imaging by co-extruding insoluble radiopaque material such as $BaSO_4$ as a component of the thermoplastic membrane.

In addition, in one embodiment, the radioopaque materials can be one or more suitable diamagnetic materials with a high atomic number. These can include compositions or salts of barium, lanthanum, lutetium, tungsten, lead, bismuth, or iodine. In addition, subject to their cost and availability osmium, gold, iridium, and other materials can be used as a radioopaque material in a fiducial marker.

Relaxation agents (such as gadolinium, Gd, $Gd^{3+}$) reduce signal intensity for T2 and increase intensity for T1. As more Gd is added, T1 becomes shorter and signal intensity increases on T1-weighted image eventually reaching a plateau and then decreasing. On T2-weighted imaging the signal is reduced immediately and is reduced further as more Gd is added. To appear bright on both T1 and T2-weighted images, a balance between the T1 enhancing property and the T2 signal loss property can be struck. The measured T1 and T2 values in the tables below and the associated figures reflect this and show the effect of increasing Gd content on T1 and T2 weighted images. In one embodiment, the levels of paramagnetic material in a given marker are adjusted such that the marker has a shortened T1 signal that is brighter on T1-weighted MRI although T2 is shortened as a consequence. In such an embodiment, T2 is not shortened enough to cause substantial signal loss on T2-weighted MRI. In one embodiment, the paramagnetic material is added to make T1 shorter (and T1-weighted MRI brighter) prior to making the T2 signal too short such that the T2-weighted signal will not appear in a given image.

The relaxation agents can be any soluble paramagnetic material. Various suitable metal ions and their complexes are recited below. Nanoparticles such as iron oxide particles or organic radicals such as the nitroxide radical can also be used.

The metal ions suitable for use as paramagnetic material for use in the marker embodiments can include, without limitation, Gd(III), Fe(III), Mn(II), Mn(III), Cr(III), Cu(II), Cu(III), Dy(III), Ho(III), Er(III), Pr(III), Eu(II), Eu(III), Nd(III), Yb(III), V(III), Sm(III), Tb(III), Tb(IV), Tm(III), V(IV), Ni(II), Co(II), Ru(III). Metal salts may be simple salts of counter ions such as nitrate, sulfate, chloride, bromide, iodide, fluoride, nitrite, sulfite, etc. Alternately, the metal used as the marker materials can be chelated by a ligand such as EDTA, DTPA, DOTA, NOTA, HEDTA, CDTA, ethylenediamine, diethylenetriamine, or other ligands described in Martell and Smith "Critical Stability Constants", Plenum Press or in the NIST Standard Reference Database of 6166 ligands.

MRI Sequences and Image Data Comparisons

Figure 6A:
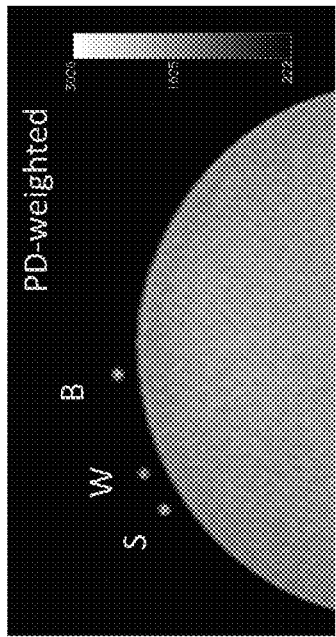
FIG. 6A shows an image of a water filled cavity having four samples disposed around the water-filled cavity obtained during a proton density weighted MRI data collection session in accordance with an illustrative embodiment of the invention.
Figure 6B:
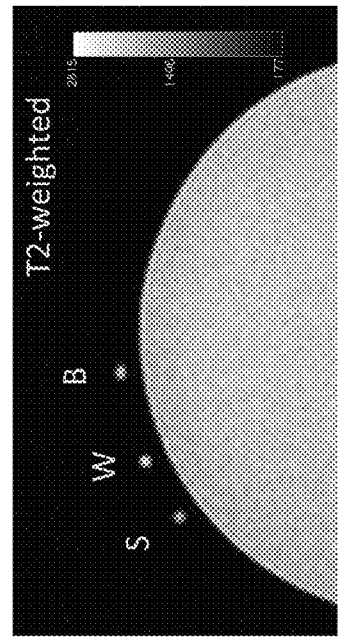
FIG. 6B shows an image of a water filled cavity having four samples disposed around the water-filled cavity obtained during a T2 weighted MRI data collection session in accordance with an illustrative embodiment of the invention.
Figure 6C:
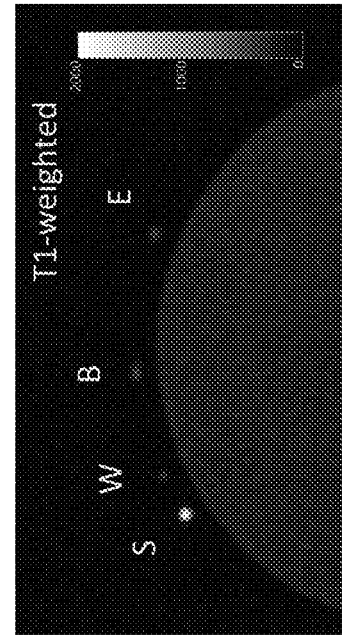
FIG. 6C shows an image of a water filled cavity having four samples disposed around the water-filled cavity obtained during a T1 weighted MRI data collection session in accordance with an illustrative embodiment of the invention.
Figure 6D:
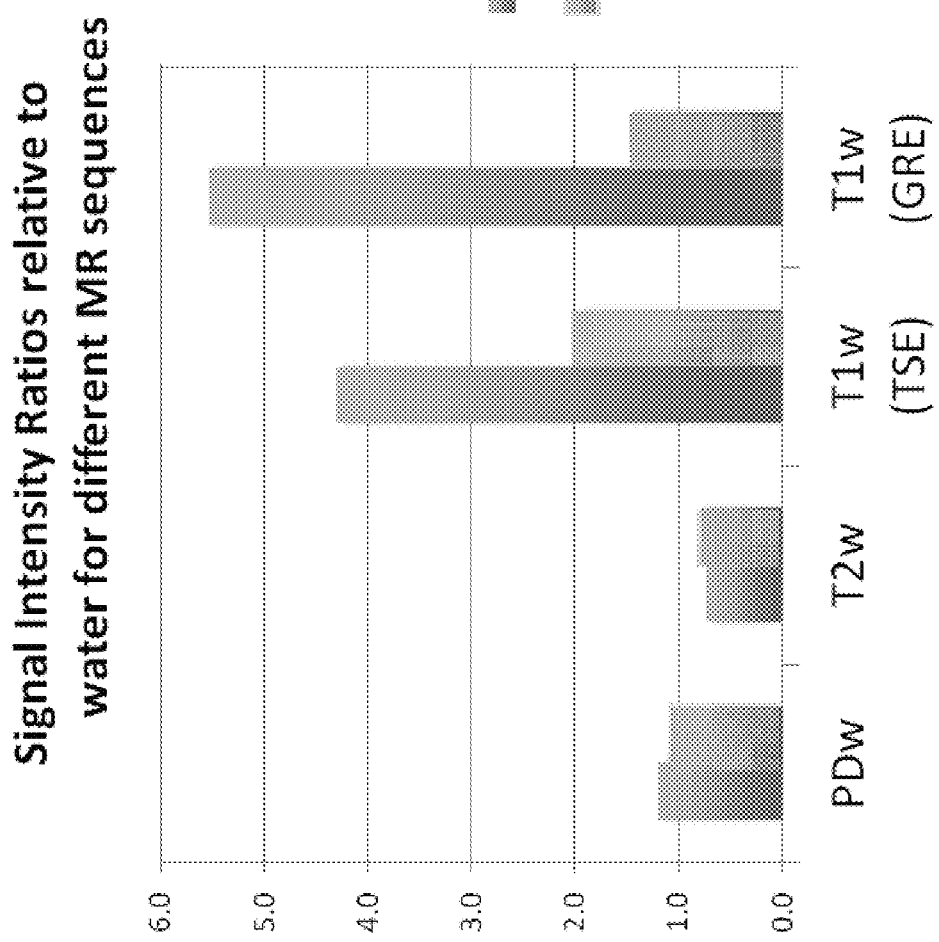
FIG. 6D is a plot comparing the signal intensity ratios for a conventional marker solution sample and a marker material relative to water in accordance with an illustrative embodiment of the invention.

FIGS. 6A-6C show images of MRI scan data obtained with respect to four samples that each contained a different solution. The samples containing a marker solution according to an embodiment of the invention is identified by S. Specifically, the marker solution using in sample S includes water and about 0.34 mg/mL Na[Gd(EDTA)], i.e. the sodium salt of the complex formed between the gadolinium(III) ion and ethylenediamine tetraacetate. A sample containing distilled deionized water is identified by W. A lipid material such as vitamin E was included in the sample identified as E. A solution from a conventional MRI marker offered by Beekley Corporation ("Beekley") (One Prestige Lane, Bristol, Conn. 06010) is identified as B or B1 in various figures discussed herein. Specifically, Beekley's MR-Spot 102 marker was used.

For some embodiments, it is useful to consider the concentration of a paramagnetic material in a given marker in terms of molarity instead of mg/mL. The three different concentrations of Gd that were used in the embodiments referenced herein were 2.7 mM, 1.3 mM, and 0.65 mM (mmol/L or millimoles per liter). For gadolinium compounds, a useful range is from about 0.01 mM to about 10 mM, but preferably between about 0.1 to about 3 mM. For a given marker embodiment, this range can vary based on composition of the gadolinium such as whether is it complexed to another ligand. For other paramagnetic compounds, the upper limit may increase to about 20 mM instead of about 10 mM.

These four samples S, W, E, and B were taped to the side of a 500 mL bottle containing distilled deionized water. With the water contained therein as a reference sample, this arrangement was scanned at 3T on a clinical scanner using standard MRI protocols. The data collected is presented as the cross-sectional images shown in FIGS. 6A-6C. MRI scans were performed on the samples and water bottle assembly using T1 weighted (FIG. 6C), T2 weighted (FIG. 6B), and proton density sequences (FIG. 6A). From each of the three figures, it is clear that the sample of the samples that includes a marker material embodiment of the invention S demonstrates a high contrast across all three figures and thus all three MRI sequences. The vitamin E sample, E, for example is not visible in the proton density weighted scan of FIG. 6A. In addition, in the T1 weighted scan, the difference between the S sample and the B sample is pronounced as shown in FIG. 6C.

Although visible inspection is likely to be a major differentiator between markers when a clinician is selecting a marker, another way to compare the marker materials in samples S, W, E, B is to evaluate the signal intensity ratios or SIRs by comparing the MRI intensity signal for each sample to that of water. Water can be used as a reference signal that can be measured during different scans and with different scan parameters such that signal intensity, noise, contrast intensity and other signals can be compared relative to signals obtained with respect to water.

In general, a signal intensity (SI) can be measured and a noise (N) signal can be measured for a given data collection session. With SI and N for a given sample, the signal to noise ratio (SNR) can be determined. A contrast intensity (CI) can also be compared to an associated noise measurement to obtain a contrast to noise ratio (CNR). In one embodiment, the CNR between two regions A and B can be defined as [SI(A)−SI(B)]/Noise. The signal to noise ratios and contrast to noise ratios were also calculated for each sample. For example, histograms plotting SIR (relative to water) for the S and B samples for the T1 weighted (TSE and GRE), T2 weighted, and proton density sequences are provided in FIG. 6D. The data for FIGS. 6A-6D is provided below in Tables 1A-5A.

For CNR, contrast level of the sample can be evaluated relative to the contrast level of pure water. As part of this evaluation, it is desirable to estimate noise as the standard deviation (SD) of the signal intensity in a region of interest in the air outside the bottle. Thus, a measurement of air in a MRI scan can be used to obtain a noise value for various signal to noise ratio calculations. An exemplary measure of CNR can be obtained as follows:

$$CNR=[(SI\ sample)-(SI\ water)]/(SD\ air).$$

For the proton density (PD) and T2-weighted scans, having a given sample have a SIR approximating that of water is the optimal result. For the T1-weighted scans, the marker material embodiment of the invention identified as S outperforms the B sample with greater SNR, greater SIR, and greater CNR values. This outcome is demonstrated using a turbo spin echo (TSE) sequence and a gradient echo (GRE) sequence referred to as VIBE.

TABLE 1A

Proton Density

| | SI | SNR | CNR (to water) | SIR (to water) |
|---|---|---|---|---|
| S | 1952 | 45.4 | 7.5 | 1.2 |
| Water (W) | 1628 | 37.9 | | |
| B | 1762 | 41.0 | 3.1 | 1.1 |
| Noise | 43 | | | |
| TR | 3810 | | | |
| TE | 39 | | | |
| Flip Angle | 90 | | | |
| Slice thickness | 1.5 | | | |

TABLE 2A

T2 TSE

| | SI | SNR | CNR (to water) | SIR (to water) |
|---|---|---|---|---|
| S | 1131 | 22 | −7.9 | 0.7 |
| Water (W) | 1540 | 30 | | |
| B | 1208 | 23 | −6.4 | 0.8 |
| Noise | 52 | | | |
| TR | 5000 | | | |
| TE | 79 | | | |
| Flip Angle | 90 | | | |
| Slice thickness | 1 | | | |

TABLE 3A

T1 TSE

| | SI | SNR | CNR (to water) | SIR (to water) |
|---|---|---|---|---|
| S | 998 | 25 | 19.2 | 4.3 |
| Water (W) | 232 | 6 | | |
| B | 462 | 12 | 5.8 | 2.0 |
| Noise | 40 | | | |
| TR | 300 | | | |
| TE | 25 | | | |
| Flip Angle | 90 | | | |
| Slice thickness | 1 | | | |

TABLE 4A

T1 VIBE

| | SI | SNR | CNR (to water) | SIR (to water) |
|---|---|---|---|---|
| S | 1290 | 99 | 81.3 | 5.5 |
| Water (W) | 233 | 18 | | |
| B | 343 | 26 | 8.5 | 1.5 |
| Noise | 13 | | | |
| TR | 7 | | | |
| TE | 2.3 | | | |
| Flip Angle | 12 | | | |
| Slice thickness | 1.5 | | | |

TABLE 5A

SIR

| | S | B |
|---|---|---|
| PDw | 1.2 | 1.1 |
| T2w | 0.7 | 0.8 |
| T1w (TSE) | 4.3 | 2.0 |
| T1w (GRE) | 5.5 | 1.5 |

TABLE 6A

| | Slice thickness = 1 mm SI | Spatial Resolution = 0.38 × 0.38 SNR | CNR | SIR (to water) |
|---|---|---|---|---|
| S | 1287 | 30 | 24.8 | 5.9 |
| Water | 220 | 5 | | |
| B | 332 | 8 | 2.6 | 1.5 |
| Vitamin E | 265 | 6 | 1.0 | 1.2 |
| Noise | 43 | | | |

TABLE 7A

| | Slice thickness = 1 mm SI | Spatial Resolution = 0.27 × 0.27 SNR | CNR | SIR (to water) |
|---|---|---|---|---|
| S | 1534 | 20 | 17.0 | 5.9 |
| Water | 260 | 3 | | |
| B | 210 | 3 | −0.7 | 0.8 |
| Vitamin E | 295 | 4 | 0.5 | 1.1 |
| Noise | 75 | | | |

TABLE 8A

| | Slice thickness = 1 mm SI | Spatial Resolution = 0.94 × 0.94 SNR | CNR | SIR (to water) |
|---|---|---|---|---|
| S | 408 | 31 | 25.0 | 4.9 |
| Water | 83 | 6 | | |
| B | 125 | 10 | 3.2 | 1.5 |
| Vitamin E | 143 | 11 | 4.6 | 1.7 |
| Noise | 13 | | | |

TABLE 9A

| | Spatial Resolution | CNR S | CNR B | CNR Vit E |
|---|---|---|---|---|
| Low Res. | 0.94 × 0.94 mm | 25.0 | 3.2 | 1.7 |
| Med Res. | 0.38 × 0.38 mm | 24.8 | 2.6 | 1.0 |
| Hi Res. | 0.27 × 0.27 mm | 17.0 | 0.8 | 0.5 |

| | | SNR S | SNR B | SNR Vit E |
|---|---|---|---|---|
| Low | 0.94 × 0.94 mm | 31 | 10 | 11 |
| Med | 0.38 × 0.38 mm | 30 | 8 | 6 |
| Hi | 0.27 × 0.27 mm | 20 | 3 | 4 |

| | | SIR S | SIR B | SIR Vitamin E |
|---|---|---|---|---|
| Low | 0.94 × 0.94 mm | 4.9 | 1.5 | 1.7 |
| Med | 0.38 × 0.38 mm | 5.9 | 1.5 | 1.2 |
| Hi | 0.27 × 0.27 mm | 5.9 | 0.8 | 1.1 |

Figure 7A:
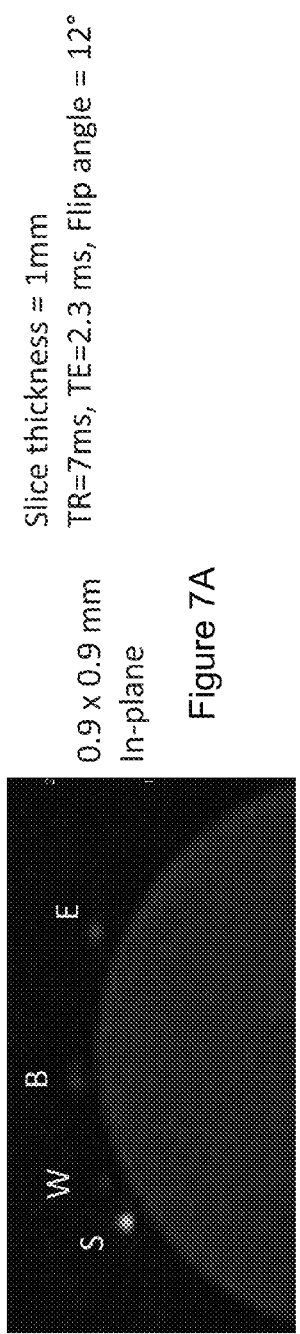
FIGS. 7A-7C show an image of a water filled cavity having four samples disposed around the water-filled cavity obtained during three T1 weighted MRI data collection sessions in which the spatial resolution increases for each subsequent scan in accordance with an illustrative embodiment of the invention.
Figure 7B:
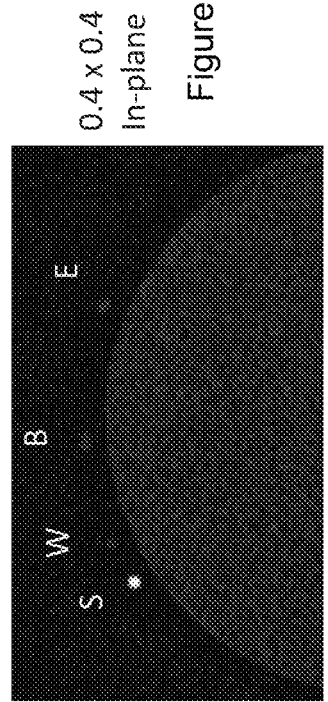
Figure 7C:
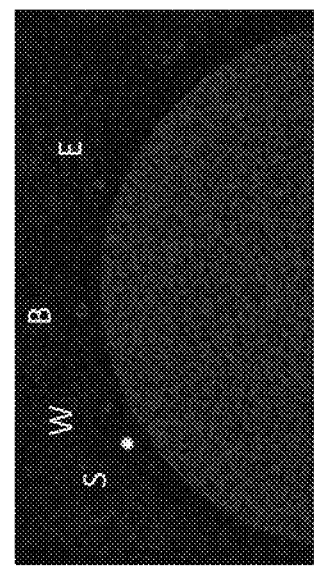

As part of the MRI scan of the four samples, the spatial resolution on the T1 Vibe images was progressively increased to show advantages with the marker material embodiment identified as S. In FIGS. 7A-7C, data obtained for the four samples S, W, E, B with a constant slice thickness of 1 mm and is shown such that the spatial resolution increases from FIG. 7A (0.94 mm by 0.94 mm in plane resolution), to FIG. 7B (0.38 mm by 0.38 mm in plane resolution) which again shows an increase in spatial resolution to FIG. 7C (0.27 mm by 0.27 mm in plane resolution;). In FIG. 7C, the S sample is still visible and sharply resolved while the other samples are barely conspicuous. In contrast, in FIG. 7C, the S sample is the brightest, but blurry given the lower resolution.

Figure 8D:
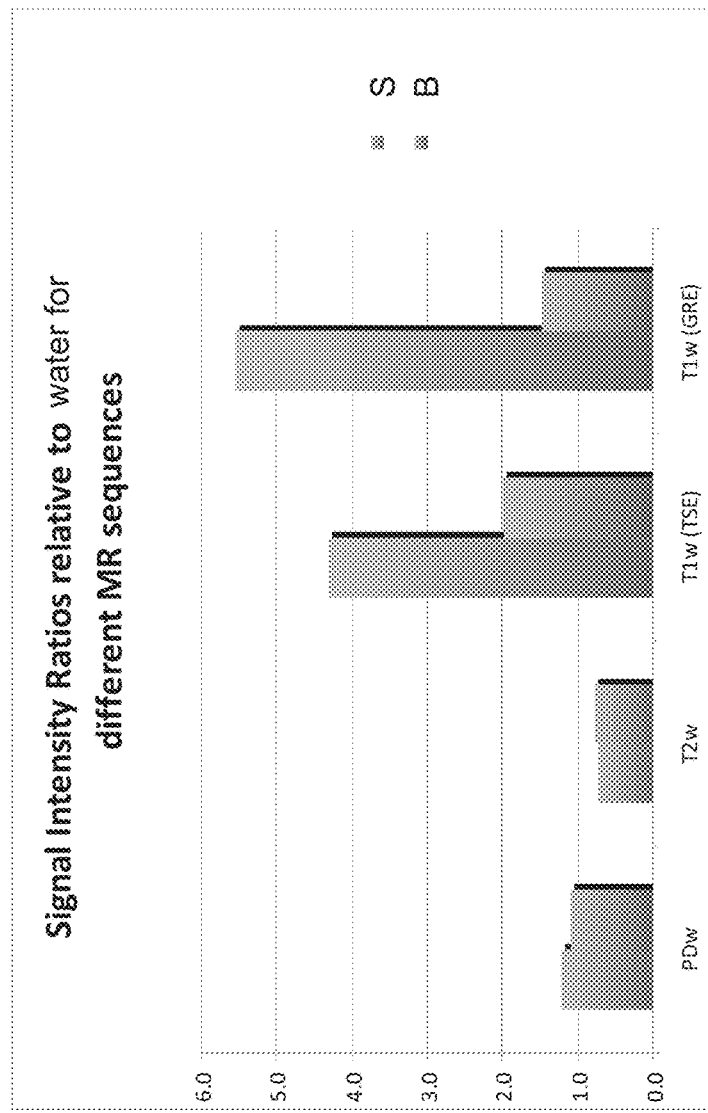
FIG. 8D is a plot of signal intensity ratios for different MRI sequences for the samples depicted in FIGS. 6A-6C and 7A-7C in accordance with an illustrative embodiment of the invention.

As resolution is increased, noise also increases. Accordingly, the Beekley and Vitamin E samples are less conspicuous on higher resolution scans relative to the S sample. This is apparent in the images and in plots of SNR, SIR, or CNR versus concentration shown in FIGS. 7A-7C and 8A-8D and in the data provided in Tables 6A-9A. In FIGS. 8A-8C, each of the three bars is grouped in order from left to right of low, medium and high resolutions using the data of Table 9A. In FIG. 8D, the S sample is on the left and the B sample is on the right.

MRI and X-Ray Sample Data for Multi-Modal Fiducial Markers

Figure 9A:
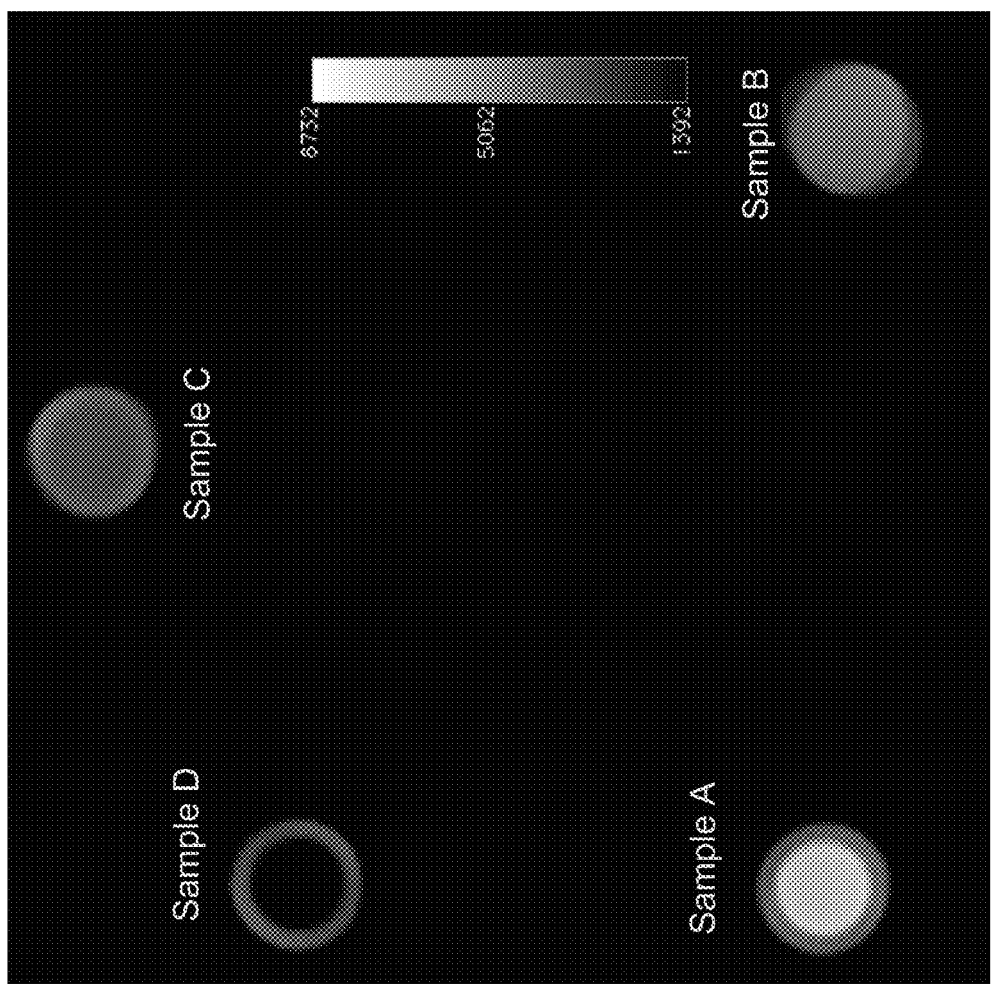
FIG. 9A shows a CT image of a water filled cavity having four samples including a marker material that includes both a paramagnetic material and a substantially radiopaque material in accordance with an illustrative embodiment of the invention.
Figure 9C:
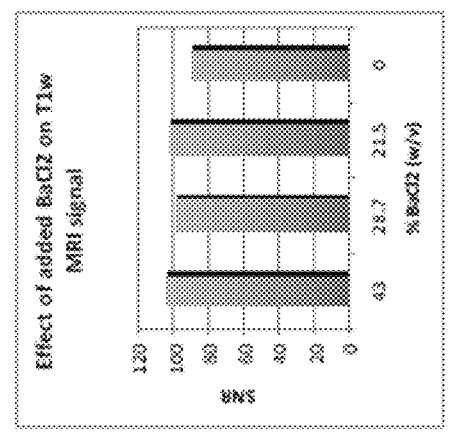
FIGS. 9B-9E show the effect of increasing levels of a substantially radiopaque material in a marker for a CT scan and three weighted MRI data collection sessions in accordance with an illustrative embodiment of the invention.
Figure 9E:
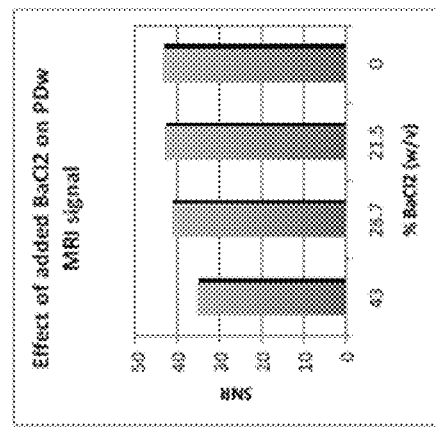
Figure 9B:
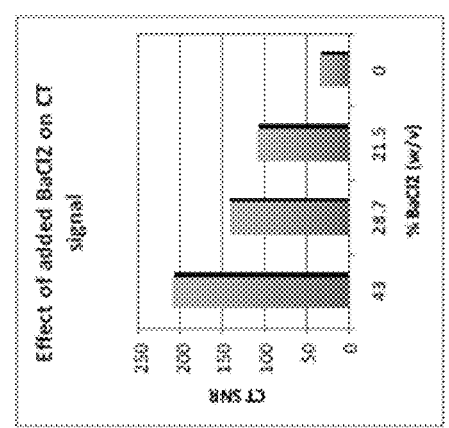
Figure 9D:
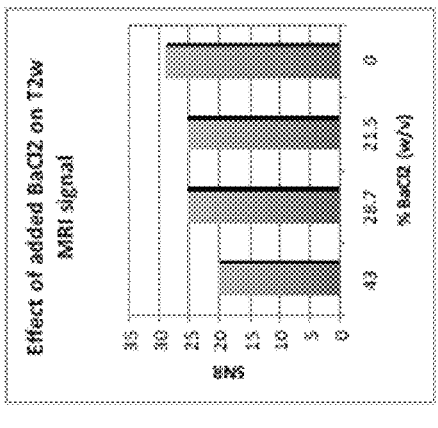

FIG. 9A shows a CT image of four samples of a marker material that includes water and a paramagnetic material according to an embodiment of the invention. The higher the amount of BaCl$_2$, in a given sample, the whiter the image. The four samples are each doped with increasing concentrations of barium chloride relative to the other samples. Thus, the concentration of BaCl$_2$ for sample A is greater than the concentration of BaCl$_2$ for sample B which is greater than the concentration of BaCl$_2$ for sample C which is greater than the concentration of sample D. Samples D, C, B, and A include about 0%, about 21.5%, about 28.7%, or about 43% BaCl$_2$ (on a weight per volume basis). As shown in FIG. 9A, the inner circular region is the sample marker material of the invention that includes BaCl$_2$, contained within the circular cross-section of the tubes containing the samples.

In general, the MR properties of samples A, B, C and D were substantially unchanged by the addition of BaCl$_2$. Table 1B provided below shows the results of a formulation in which increasing amounts of barium chloride were added to the material used in MR sample S. As expected, a linear increase in CT intensity occurs as a function of added barium. An unexpected result is that for concentrations of about 21.5%, about 28.7%, or about 43% of BaCl$_2$.2H$_2$O, the MR performance of the marker embodiments of the invention are not perturbed. The SNR for T1, T2, and proton density weighted images is nearly the same for each sample.

In one embodiment, the marker material or marker can include between greater than 0% and less than about 50% BaCl$_2$.2H$_2$O, on a weight per volume basis. In another embodiment, the marker material or marker can include between greater than about 20% and less than about 45% BaCl$_2$.2H$_2$O, on a weight per volume basis. The BaCl$_2$ is dissolved in water to form an aqueous solution in one embodiment. Such an aqueous solution can also include gadolinium and other materials or solvents such as 0.65 mM Na[Gd(EDTA)] to form a marker solution suitable for filling a membrane having a flexible tube, disk, sphere or other geometry. EDTA or Ethylenediaminetetraacetic acid can be used to maintain solubility of Gd at neutral pH. In tables 1B and 2B, data relating to a set of CT scans and MRI scans is used to generate FIGS. 9A-9E. These figures plot CT SNR and MRI SNI with different amounts of BaCl$_2$.2H$_2$O in the marker material or solution.

TABLE 1B

MRI DATA FOR DIFFERENT %'s of BaCl$_2$ •2H$_2$O

| T1 SI | T1 SNR | T2 SI | T2 SNR | PD SI | PD SNR | % BaCl2•2H2O |
|-------|--------|-------|--------|-------|--------|--------------|
| 1784  | 104.9  | 1022  | 20.4   | 1496  | 35.6   | 43           |
| 1674  | 98.5   | 1275  | 25.5   | 1744  | 41.5   | 28.7         |
| 1746  | 102.7  | 1282  | 25.6   | 1820  | 43.3   | 21.5         |
| 1530  | 90.0   | 1458  | 29.2   | 1830  | 43.6   | 0            |
| Noise |        | Noise |        | Noise |        |              |
| 17    |        | 50    |        | 42    |        |              |

TABLE 2B

CT DATA FOR DIFFERENT %'s of BaCl$_2$ · 2H$_2$O

|            | CT SI | CT SNR |
|------------|-------|--------|
| % BaCl$_2$ · 2H$_2$O | | |
| 43         | 6695  | 211    |
| 28.7       | 4554  | 144    |
| 21.5       | 3470  | 109    |
| 0          | 1129  | 36     |
| CT Noise   |       |        |
| 31.7       |       |        |

In addition to the experiments describes above, additional trials were performed with respect to various marker material formulations relative to conventional markers. T1, T2, and proton density (PD) weighted images are the most common images generated using MRI. Various markers based upon the designs described herein having different concentrations of gadolinium-based aqueous marker solutions were tested relative to a doped water sample to evaluate the strength of each marker's signal and the associated signal to noise ratio. Distilled deionized water was used in the trials discussed above with respect to FIGS. 6A-6C and 7A-7C.

Figure 10A:
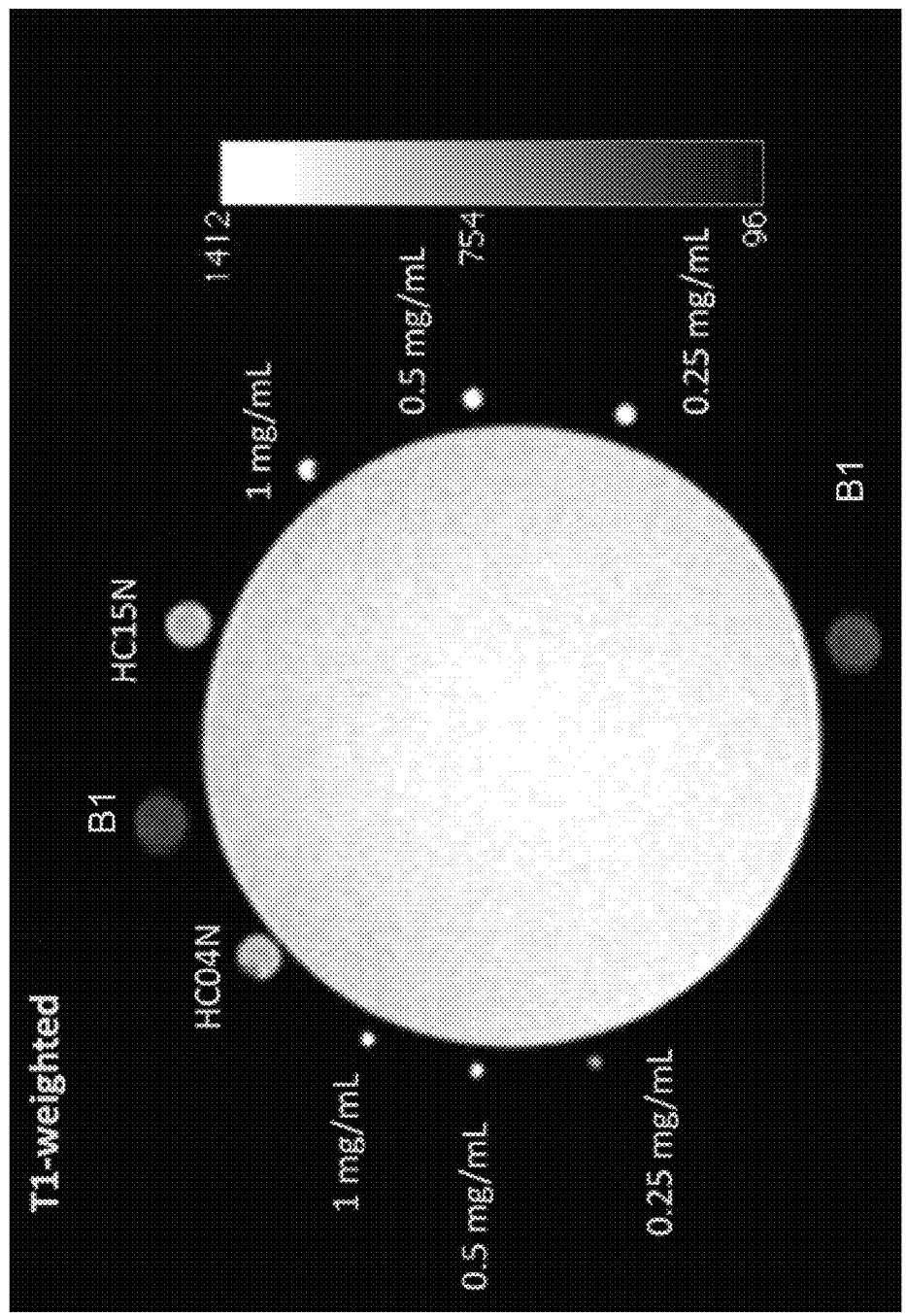
FIG. 10A shows an image of a water filled cavity having a plurality of fiducial markers disposed around the water-filled cavity obtained during a T1 weighted MRI data collection session in accordance with an illustrative embodiment of the invention.
Figure 10B:
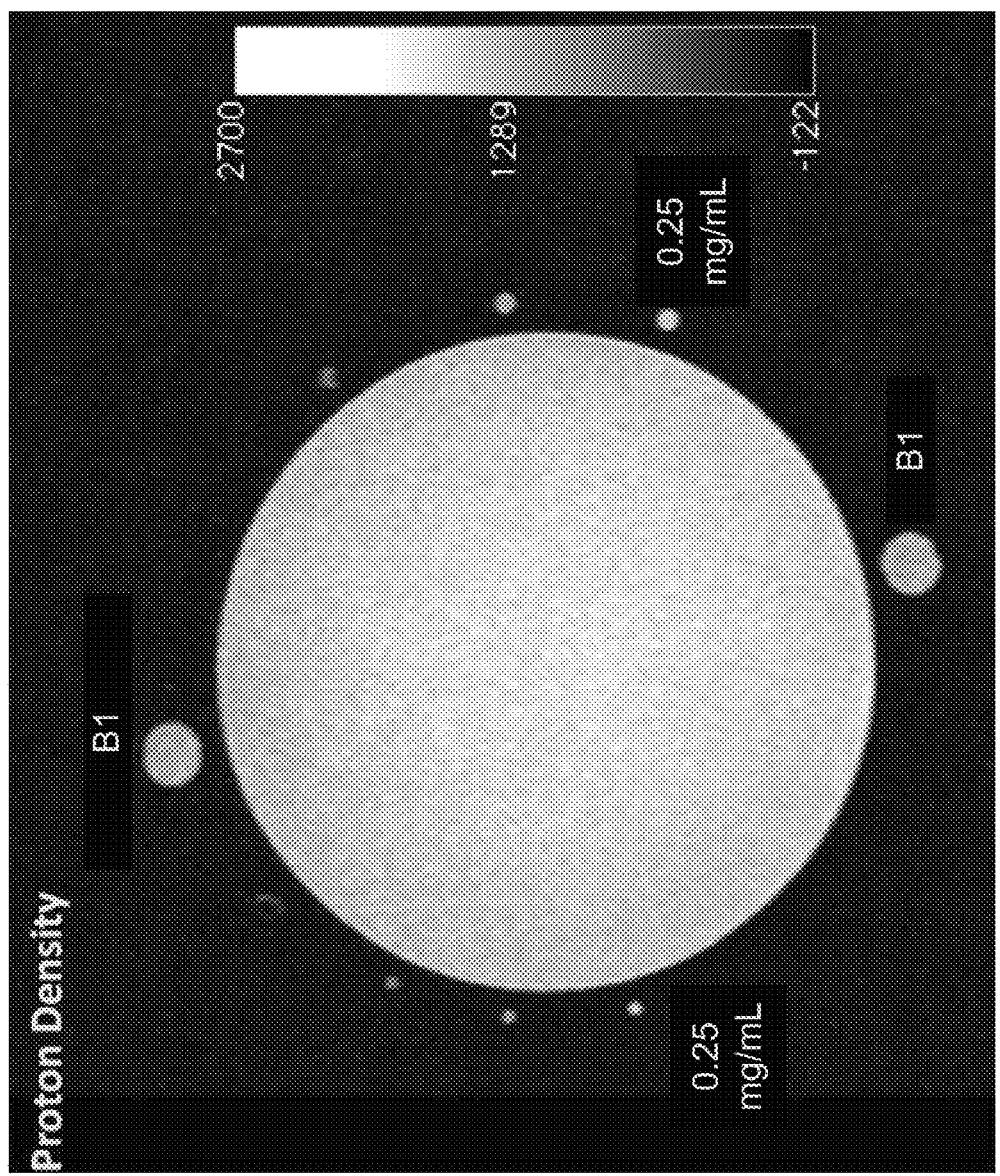
FIG. 10B shows an image of a water filled cavity having a plurality of fiducial markers disposed around the water-filled cavity obtained during a proton density MRI data collection session in accordance with an illustrative embodiment of the invention.
Figure 10C:
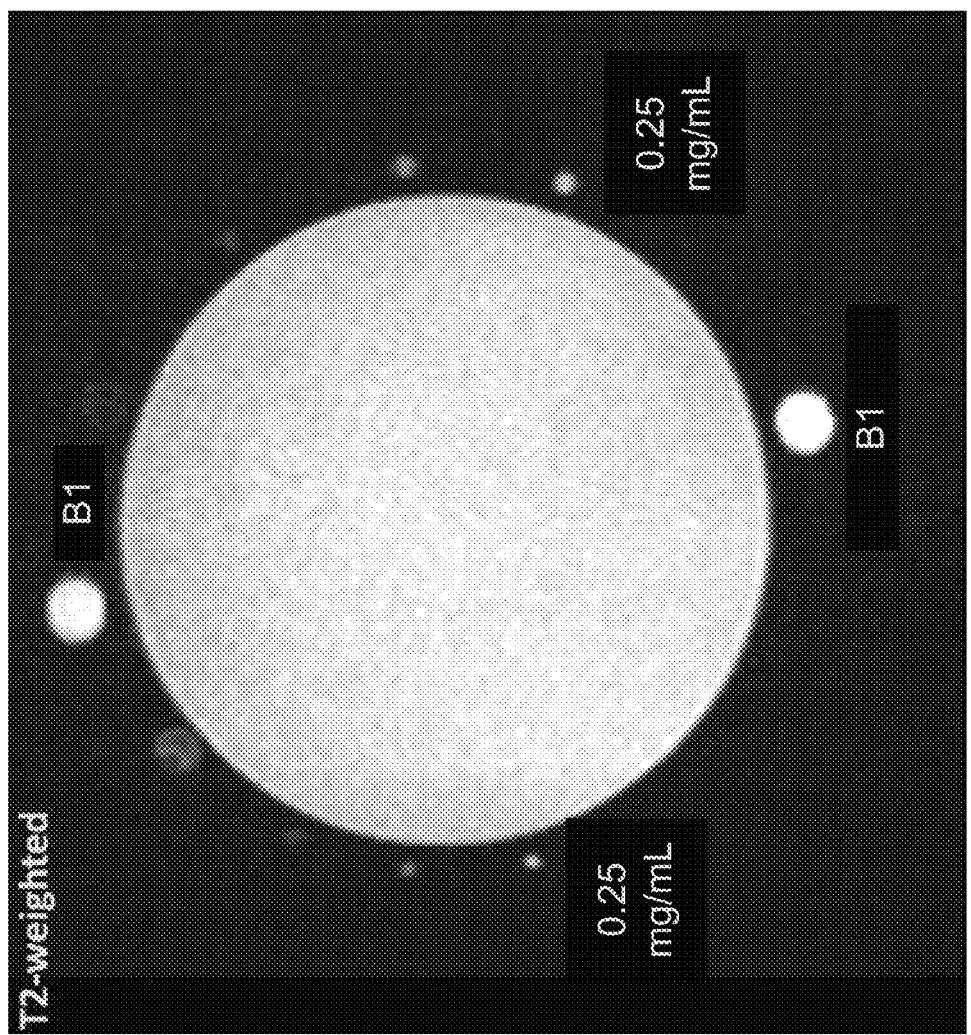
FIG. 10C shows an image of a water filled cavity having a plurality of fiducial markers disposed around the water-filled cavity obtained during a T2 weighted data MRI collection session in accordance with an illustrative embodiment of the invention.
Figure 11A:
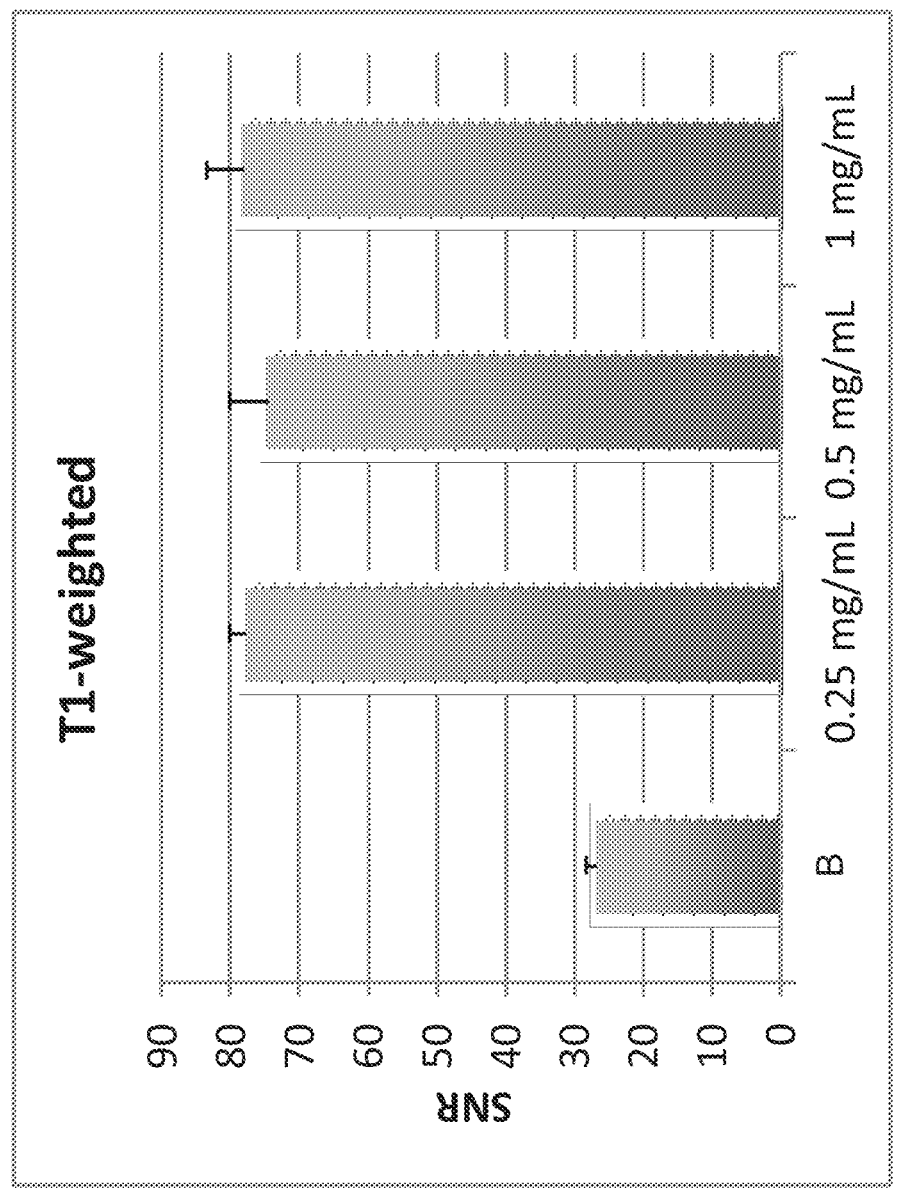
FIG. 11A shows a bar chart depicting the signal to noise ratios of some of the fiducial markers shown in FIG. 10A in accordance with an illustrative embodiment of the invention.
Figure 11B:
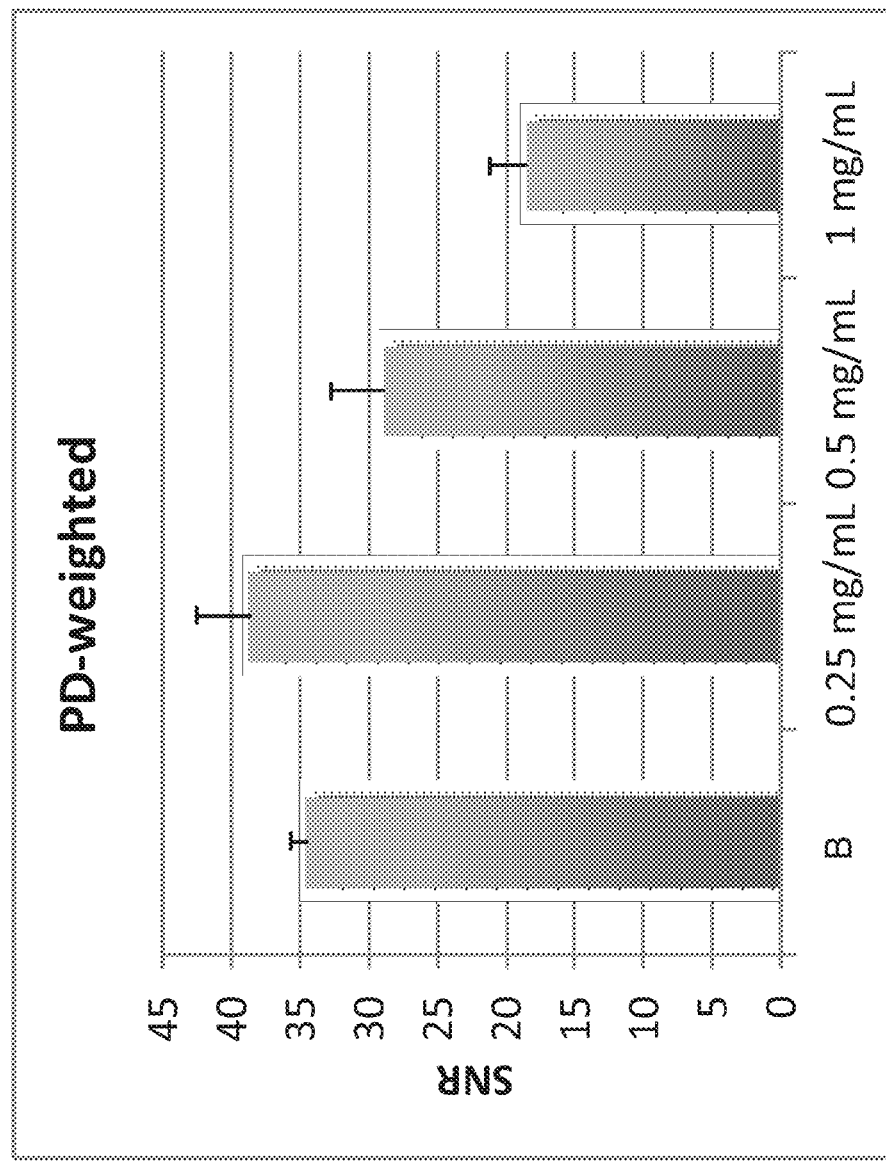
FIG. 11B shows a bar chart depicting the signal to noise ratios of some of the fiducial markers shown in FIG. 10B in accordance with an illustrative embodiment of the invention.
Figure 11C:
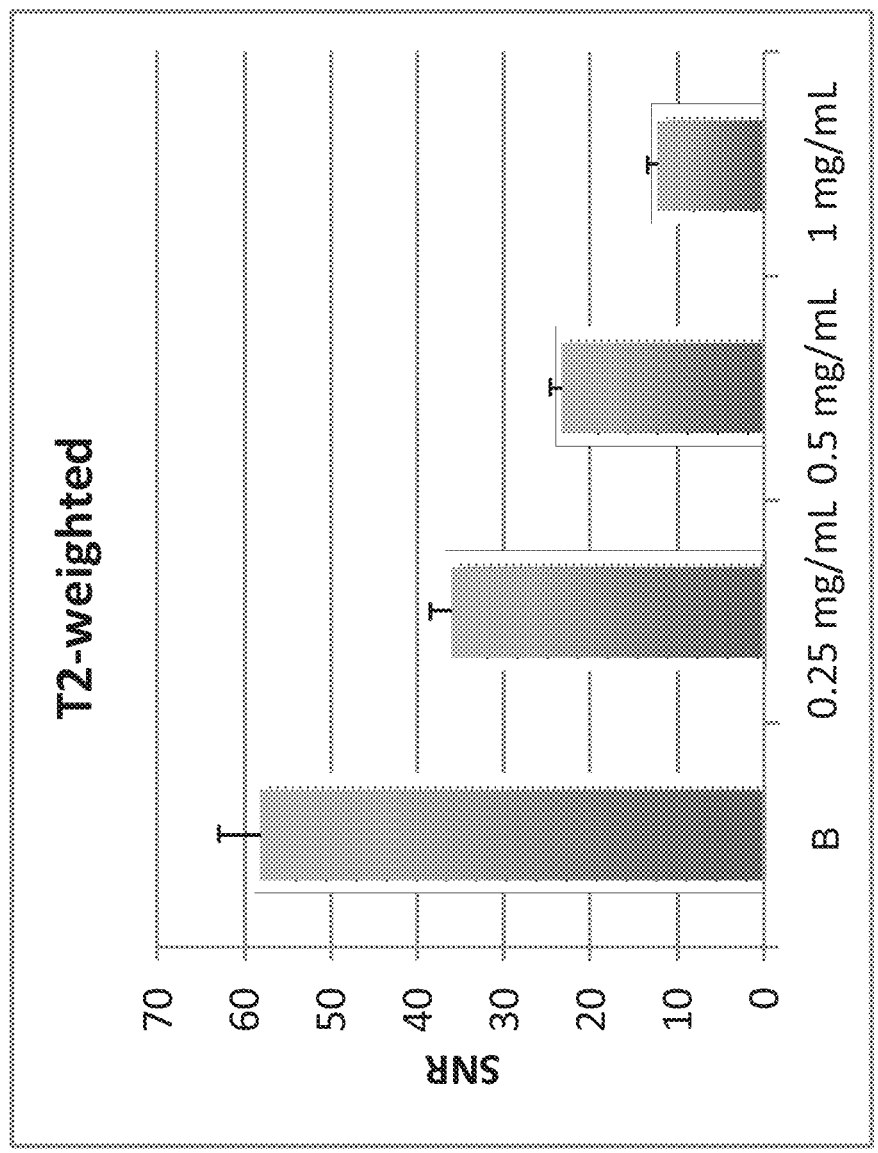
FIG. 11C shows a bar chart depicting the signal to noise ratios of some of the fiducial markers shown in FIG. 10C in accordance with an illustrative embodiment of the invention.

With respect to the images shown in FIGS. 10A-10C and 11A-11C, the water was doped with was doped with a paramagnetic material to make it bright for the T1 weighted session. The same marker embodiments and two conventional markers were imaged three different times in the same arrangement using T1, T2, and proton density (PD) MRI sequences. These images are shown in FIGS. 10A-10C and the signal to noise ratio of the conventional marker, B, sold by Beekley and the marker embodiments having a membrane containing about 0.65 mM of Na[Gd(EDTA)] in water, about 1.3 mM of Na[Gd(EDTA)] in water and about 2.7 mM of Na[Gd(EDTA)] in water are plotted in FIGS. 11A-11C.

In FIGS. 10A-10C, the large central circle is a water bottle with the commercial markers B at the top and bottom. The marker embodiments of the invention with a solution of soluble paramagnetic material are shown around the left and right halves of the circle. The three images of FIGS. 10A-10C show the improvement of a 0.65 mM Na[Gd(EDTA)]-based marker over the B marker in the T1 image and similar signal to marker B in Proton Density and T2 images. As shown in FIG. 10A, in T1 weighted imaging, membrane-filled marker embodiments are substantially isointense with each other and notably more intense than an available commercial marker B. The HC04N and HC15N items in the image are polyethylene gel-based materials made by Cosmo Instruments (Japan).

Based on these figures and the data included below in tables 1, 2, and 3, the signal intensity of the marker embodiments are demonstrated to have improved MRI imaging characteristics over commercially available MRI markers, such as the B marker. In part, the markers are improved by the addition of trace amounts of gadolinium. Tests show a preferred concentration for substantially maximized signal on the T1 weighted, T2 weighted, and proton density sequences to be about 0.65 mM Na[Gd(EDTA)], although this may be varied to increase signal for one of the specific imaging sequences. This concentration significantly enhances the T1 signal without significantly diminishing the T2 signal, both of which are routine components of medical MRI imaging studies. Images are attached showing ⅟16" ID (left) and 3.32" ID (right) markers at 0.65 mM Na[Gd(EDTA)], 1.3 mM Na[Gd(EDTA)], and 2.7 mM Na[Gd(EDTA)] and using the B1 marker as a reference.

Tables 1C, 2C, and 3C referenced below include the T1 and T2 values for the commercial marker B and three prototype markers having increasing Gd concentration. These are absolute numbers and can be compared to other data. Also in the tables are the signal intensities and signal to noise ratios for these four fiducial markers when measured using T1-, T2-, or proton density (PD)-weighted scans. The SNR values can be compared across all scans. In one embodiment, signal intensity values can be compared within a single scan. However, signal intensity values can vary for the same marker across different scans. Accordingly, because SNR can be used as a comparable that is on the same scale across the scans.

The data collected in tables 1C, 2C, and 3C and the images generated in FIGS. 10A, 10B, and 10C were obtained with the following settings:
Imaging Performed at 3T
T1-Weighted Imaging
TR=7 ms, TE=2.3 ms, flip angle=12°, field of view (FOV)=120×120 mm, resolution=0.23×0.23×1.5 mm
T2-Weighted Imaging
TR=4330 ms, TE=101 ms, flip angle=90°, field of view (FOV)=140×140 mm, resolution=0.44×0.44×1.5 mm
PD-Weighted Imaging
TR=3810 ms, TE=39 ms, flip angle=90°, field of view (FOV)=120×120 mm, resolution=0.19×0.19×1.5 mm Two main types of sequences used in MRI (and many variants on these) are described below in terms various inter-related MRI relationships:
Spin Echo
Signal, $S=\rho[1-\exp(-TR/T1)]\times[\exp(-TE/T2)]$
and Gradient Echo
Signal, $S=\rho[(1-\exp(-TR/T1))\times\sin(FA)/(1-\exp(-TR/T1)\times\cos(FA))]\times[\exp(-TE/T2^*)]$
Where $\rho$=the proton density, this is the maximum signal that can be detected
TR=the repetition time, this is set by the scanner operator
TE=the echo time, set by the scanner operator
FA=flip angle, also set by the scanner operator
T1=longitudinal relaxation time, an inherent property of the tissue or sample
T2=transverse relaxation time, an inherent property of the tissue or sample
T2*=susceptibility relaxation time, an inherent property of the tissue or sample
By changing TR, TE, and FA, the scan can be changed such that it is T1-, T2-, or proton density weighted.
For T1 weighted, TR should be short, FA should be low, and TE<<T2 or T2*
For T2 weighted, TR>T1, long TE
For proton density, long TR (>T1) and short TE
In T1-weighted images, tissue or samples with short T1 appear bright.
In T2-weighted images, tissue or samples with long T2 appear bright.

TABLE 1C

| | T1 (ms) | T2 (ms) | Noise 15.5 Signal Intensity T1-weighted | Std dev | SNR |
|---|---|---|---|---|---|
| B1 | 959 | 764 | 416 | 22 | 27 |
| 0.25 mg/mL | 294 | 240 | 1204 | 35 | 78 |
| 0.5 mg/mL | 123 | 102 | 1155 | 86 | 75 |
| 1 mg/mL | 78 | 66 | 1210 | 80 | 78 |

TABLE 2C

| | T1 (ms) | T2 (ms) | Noise 25.4 Signal Intensity T2-weighted | Std dev | SNR |
|---|---|---|---|---|---|
| B1 | 959 | 764 | 1475 | 125 | 58 |
| 0.25 mg/mL | 294 | 240 | 916 | 63 | 36 |
| 0.5 mg/mL | 123 | 102 | 592 | 32 | 23 |
| 1 mg/mL | 78 | 66 | 311 | 30 | 12 |

TABLE 3C

| | T1 (ms) | T2 (ms) | Noise 39.0 Signal Intensity PD-weighted | Std dev | SNR |
|---|---|---|---|---|---|
| B1 | 959 | 764 | 1346 | 47 | 34 |
| 0.25 mg/mL | 294 | 240 | 1508 | 150 | 39 |
| 0.5 mg/mL | 123 | 102 | 1124 | 157 | 29 |
| 1 mg/mL | 78 | 66 | 722 | 104 | 19 |

The following examples are provided for illustration, not limitation.

EXAMPLES

1. A length of marker tubing about 12-18" long and ⅜" in diameter can be used to indicate the site of interest along the lateral abdomen and low back during imaging.
2. A length about 2" long and ¼" diameter can be used to mark tenderness at the posterior knee.
3. A length 4" long and 3/32" diameter can be used to mark a breast tumor. Adhesive is applied directly to the tubing, to the tape, or not used at all (as in the example of a gastrointestinal MRI marker designed to be swallowed).
4. In one embodiment, the membrane includes Flexelene and is manufactured by Eldon James Corporation, Colorado and/or C-Flex manufactured by Saint-Gobain.

The aspects, embodiments, features, and examples of the invention are to be considered illustrative in all respects and are not intended to limit the invention, the scope of which is defined only by the claims. Other embodiments, modifications, and usages will be apparent to those skilled in the art without departing from the spirit and scope of the claimed invention.

The use of headings and sections in the application is not meant to limit the invention; each section can apply to any aspect, embodiment, or feature of the invention.

Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" is before a quantitative value, the present teachings also include the specific quantitative value itself, unless specifically stated otherwise. As used herein, the term "about" refers to a ±10% variation from the nominal value.

It should be understood that the order of steps or order for performing certain actions is immaterial so long as the present teachings remain operable. Moreover, two or more steps or actions may be conducted simultaneously.

Where a range or list of values is provided, each intervening value between the upper and lower limits of that range or list of values is individually contemplated and is encompassed within the invention as if each value were specifically enumerated herein. In addition, smaller ranges between and including the upper and lower limits of a given range are contemplated and encompassed within the invention. The listing of exemplary values or ranges is not a disclaimer of other values or ranges between and including the upper and lower limits of a given range.

Furthermore, whereas particular embodiments of the invention have been described herein for the purpose of illustrating the invention and not for the purpose of limiting the same, it will be appreciated by those of ordinary skill in the art that numerous variations of the details, materials and arrangement of elements, steps, structures, and/or parts may be made within the principle and scope of the invention without departing from the invention as described in the claims.

What is claimed is:

1. A non-invasive fiducial marker comprising:
a first flexible membrane having a thickness (M);
an elongate cavity defined by the first flexible membrane having a volume (V); and
an aqueous solution including a concentration of paramagnetic material sufficient to increase a signal to noise ratio of the marker in an image and a substantially radiopaque material, the aqueous solution disposed in and substantially filling the elongate cavity, the aqueous solution filled elongate cavity having an interior three-dimensional shape including a length (L), a width (W), and a height (H), wherein the first flexible membrane comprises a first sealed end and a second sealed end, wherein each of the first sealed end and the second sealed end tapers to a substantially aqueous solution-free region of the first flexible membrane.

2. The non-invasive fiducial marker of claim 1 wherein the aqueous solution is configured to have a signal intensity ratio of an intensity signal of the fiducial marker relative to an intensity signal of water greater than about 2 during at least one MRI sequence.

3. The non-invasive fiducial marker of claim 2 wherein the MRI sequence is selected from the group consisting of a T1 weighted sequence, a T2 weighted sequence, and a proton density sequence.

4. The non-invasive fiducial marker of claim 3 wherein the signal intensity ratio of the intensity signal of the fiducial marker relative to the intensity signal of water is greater than about 1.1 during a proton density weighted MRI sequence.

5. The non-invasive fiducial marker of claim 1 wherein the paramagnetic material comprises gadolinium and the aqueous solution has a concentration of gadolinium that ranges from about 0.01 mM to about 10 mM.

6. The non-invasive fiducial marker of claim 1 wherein the paramagnetic material comprises gadolinium and the aqueous solution has a concentration of gadolinium of about 2.7 mM, about 1.3 mM, or about 0.65 mM.

7. The non-invasive fiducial marker of claim 2 further comprising a second elongate cavity defined by the first flexible membrane and a terminal seal formed from the first flexible membrane, wherein the second cavity is substantially filled with the aqueous solution, wherein the second cavity is adjacent to and releasably connected to the terminal seal.

8. The non-invasive fiducial marker of claim 7 further comprising an elongated substrate wherein the first flexible membrane is attached to a plurality of equally spaced regions of the elongate substrate.

9. The non-invasive fiducial marker of claim 1 further comprising a MRI imaging solution and a second flexible membrane, wherein second flexible membrane is substantially adjacent to the first flexible membrane.

10. The non-invasive fiducial marker of claim 1 further comprising a hole configured to receive a needle, wherein the hole is defined by the first flexible membrane.

11. The non-invasive fiducial marker of claim 1 further comprising a plurality of cavities, linked together by a plurality of sealed sections of the first flexible membrane such that the plurality of cavities are substantially co-linear, the plurality of cavities being substantially filled with the aqueous solution and having substantially the same dimensions V, W, L and H.

12. The non-invasive fiducial marker of claim 1 wherein the marker has a shape and wherein the shape is selected from the group consisting of substantially cylindrical, substantially toroidial, substantially spherical, substantially tubular, substantially polyhedronic, substantially rectangular, substantially pyramidal, substantially conical, a conic section, substantially cubic, substantially triangular, substantially circular, substantially square, substantially rectangular, substantially trapezoidal, irregular, arctuate, and substantially cylindrical.

13. The non-invasive fiducial marker of claim 1 wherein M ranges from about 0.010" to about 0.050"; L ranges from about 0.2 cm to about 30.0 cm; W ranges from about 0.1 cm to about 1.5 cm; and H ranges from about 0.1 cm to about 1.5 cm.

14. The non-invasive fiducial marker of claim 1 wherein M is about 0.031"; wherein L is about 0.5 cm wherein W is about 1.6 mm; and H is about 1.6 mm.

15. The non-invasive fiducial marker of claim 1 wherein the first flexible membrane comprises thermoplastic elastomer.

16. The non-invasive fiducial marker of claim 1 wherein the aqueous solution filled cavity is selected from the group consisting of substantially spherical, elongated and substantially cylindrical, and elongated and substantially rectangular.

17. The non-invasive fiducial marker of claim 1 further comprising a substrate comprising a support layer and a pressure sensitive adhesive layer disposed below the support layer wherein the first flexible membrane is attached to the support layer.

18. The non-invasive fiducial marker of claim 1 wherein the aqueous solution is configured to have a first signal intensity ratio relative to water that is greater than a second signal intensity ratio relative to water of a reference marker in at least one MRI sequence.

19. The non-invasive fiducial marker of claim 18 wherein the reference marker is selected from the group consisting of a marker comprising water; a marker comprising an alcohol; a marker comprising a lipid; a marker comprising a substantially metal-free marker; a substantially paramagnetic material-free marker; a marker consisting of water; a marker consisting of an alcohol; a marker consisting of a lipid; a marker consisting essentially of water; a marker consisting essentially of an alcohol; and a marker consisting essentially of a lipid.

20. The non-invasive fiducial marker of claim 1 wherein the elongate cavity is substantially free of one or more visible bubbles.

21. The non-invasive fiducial marker of claim 1 wherein the fiducial marker has a signal intensity ratio relative to water that is greater than about 2 and less than about 6 for a T1 weighted MRI scan.

22. The non-invasive fiducial marker of claim 1 wherein at least two of the length (L), the width (W), and the height (H) are substantially equal.

23. The non-invasive fiducial marker of claim 1 wherein the substantially radiopaque material comprises $BaCl_2.2H_7O$.

24. A non-invasive fiducial marker comprising:
a flexible membrane having a thickness (M);
a cavity defined by the flexible membrane having a volume (V); and
an aqueous solution comprising a substantially radiopaque material and a concentration of paramagnetic material sufficient to increase a signal to noise ratio of the marker in an image, the aqueous solution disposed in and substantially filling the cavity, the aqueous solution filled cavity having an interior three-dimensional shape including a length (L), a width (W), and a height (H), wherein the substantially radiopaque material comprises $BaCl_2.2H_2O$, wherein the concentration of $BaCl_2.2H_2O$ by weight per unit volume ranges from greater than about 0% to less than about 50%.

* * * * *